(12) United States Patent
Igarashi et al.

(10) Patent No.: US 7,173,033 B2
(45) Date of Patent: Feb. 6, 2007

(54) NITROGEN-CONTAINING HETEROCYCLIC COMPOUND

(75) Inventors: Susumu Igarashi, Tsukuba (JP); Ryo Naito, Tsukuba (JP); Yoshinori Okamoto, Tsukuba (JP); Noriyuki Kawano, Tsukuba (JP); Issei Tsukamoto, Tsukuba (JP); Ippei Sato, Tsukuba (JP); Makoto Takeuchi, Tsukuba (JP); Hiroyuki Kanoh, Itabashi-ku (JP); Masato Kobori, Tsukuba (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 11/190,859

(22) Filed: Jul. 28, 2005

(65) Prior Publication Data

US 2005/0261297 A1    Nov. 24, 2005

Related U.S. Application Data

(63) Continuation of application No. 10/505,939, filed as application No. PCT/JP03/02248 on Feb. 27, 2003, now abandoned.

(30) Foreign Application Priority Data

Mar. 1, 2002    (JP) .......................... P. 2002-56209

(51) Int. Cl.
*C07D 487/04* (2006.01)
*A61K 31/5025* (2006.01)
*A61P 19/08* (2006.01)

(52) U.S. Cl. ...................... 514/248; 540/481; 540/599; 544/236; 514/217.06

(58) Field of Classification Search ................ 544/236; 514/248, 217.06; 540/481, 599
See application file for complete search history.

(56) References Cited

U.S. PATENT DOCUMENTS 3,957,766 A    5/1976    Berger et al.

FOREIGN PATENT DOCUMENTS

| DE | 2 161 586 | 12/1971 |
|---|---|---|
| DE | 2 161 587 | 12/1971 |
| DE | 2 215 999 | 4/1972 |
| DE | 2 113 438 | 9/1972 |
| DE | 2 254 873 | 11/1972 |
| DE | 2 261 693 | 12/1972 |
| DE | 24 44 322 | 9/1974 |
| EP | 1 277 754 A1 | 1/2003 |
| JP | 50-58092 | 5/1975 |
| WO | WO 00/59484 A | 10/2000 |
| WO | WO 01/83481 A1 | 11/2001 |

OTHER PUBLICATIONS

Legraverend et al. *J. Heterocyclic Chem.*, 18, 893-898 (1981).*
Parravicini et al., "Derivati Della 3-Idrazinopiridazina", *Farmaco. Ed. Sci.*, 34(4), 299-310 (1979).
Tabak et al., "Steric Effects in 1-Phenyl-5-substituted Pyrazoles", *Tetrahedron*, 22(7), 2703-9 (1966).

* cited by examiner

*Primary Examiner*—Kahsay Habte
(74) *Attorney, Agent, or Firm*—Sughrue Mion, PLLC

(57) ABSTRACT

As a result of an effort made by us for the purpose of developing a therapeutic agent having a bone formation-stimulating effect by promoting the functions of osteoblasts, the present inventors discovered that a certain nitrogen-containing heterocyclic compound exhibits a potent bone formation-stimulating effect on the osteoblast and thus can serve as an excellent prophylactic or therapeutic agent against a metabolic bone disease, whereby establishing the present invention.

Thus, the present invention provides a 3,6-disubstituted 1,2,4-triazolo[4,3-b]pyridazine compound or a pharmaceutically acceptable salt thereof as well as a pharmaceutical composition comprising such a compound and a pharmaceutically acceptable carrier, especially a bone-forming agent.

7 Claims, 1 Drawing Sheet

NITROGEN-CONTAINING HETEROCYCLIC COMPOUND

This is a continuation of application Ser. No. 10/505,939 filed Aug. 30, 2004, now abandoned which is a U.S. national stage entry of PCT/JP03/02248, filed Feb. 27, 2003. The entire disclosures of the prior applications, application Ser Nos. 10/505,939 and PCT/JP03/02248 are hereby incorporated by reference.

TECHNICAL FIELD

The present invention relates to a nitrogen-containing heterocyclic compound having an ability of stimulating bone formation in an osteoblast or a pharmaceutically acceptable salt thereof.

BACKGROUND ART

A normal bone metabolism involves an equilibrium between the level of bone resorption by osteoclasts and the level of bone formation by osteoblasts, by which a homeostasis is maintained. A metabolic bone disease is considered to be developed once such a balance between the bone resorption and the bone formation is lost. This disease includes osteoporosis, osteitis fibrosa (hyperparathyroidism), osteomalacia and Paget's disease which affects the parameters of systemic bone metabolism. The osteoporosis is observed frequently in postmenoposal women or old men, and causes a pain such as a lumbar pain and a bone fracture, and is seriously problematic especially in older patients whose bone fracture readily leads to a systemic weakness and a dementia. For the purpose of treating or preventing such a bone disease, a calcium preparation, active vitamin $D_3$ preparation, calcitonin preparation and estrogen preparation are employed.

However, most of these therapeutic agents do not exhibit marked bone formation-stimulating effect, although they were reported to have a bone resorption-inhibiting effect. A bone-forming agent is highly desired especially in a senile osteoporosis which was reported to be caused mainly by a reduction in the bone formation due to a reduction in the bone turnover (New Eng. J. Med. 314, P1676, (1986)).

Recently, a benzothiepin derivative (for example, JP-A-8-231569) and an N-quinolylanthranilic acid derivative (for example; JP-A-9-188665) having an alkaline phosphatase-inducing activity were reported to be useful in promoting osteogenesis and in treating a metabolic bone disease. Nevertheless, their clinical utility is unknown.

On the other hand, there are the following reports with regard to triazolopyridazine derivatives (symbols in the description represent the symbols in Formula (I) of the invention described below). However, any of these references and patent specifications does not contain any disclosure or suggestion of an osteogenesis-promoting effect.

(1) An antibacterial compound wherein Ra and Rb are taken together with an adjacent N atom to form a piperidino, E is a single bond, and R is piperidino disclosed in U.S. Pat. No. 3,957,766; a method for synthesizing a compound wherein R is an unsubstituted phenyl disclosed in Tetrahedron, 22(7), 2073–9 (1966); a structure of a compound wherein R is p-(trifluoromethyl)phenyl or p-chlorophenyl disclosed in CAS Registry File under the codes RN=289651-67-8 and 202820-26-6; and a compound wherein R is o-nitrophenyl disclosed in SPECS catalog under Refcode:AG-690/3073051.

(2) A triazolopyridazine derivative having a bronchodilating effect which is a compound wherein Ra and Rb are taken together with an adjacent N atom to form a 4-methyl-1-piperazinyl, E is a single bond, and R is an unsubstituted phenyl, p-methylphenyl, m-methylphenyl, p-methoxyphenyl, m-chlorophenyl, p-chlorophenyl or m-nitrophenyl, disclosed in German Patent 2,444,322 and JP-A-50-58092.

(3) An antibacterial compound wherein R is an optionally substituted imidazolyl disclosed in German Patents 2,261, 693, 2,254,873 and 2,215,999; an antibacterial compound wherein R is 5-nitro-2-furyl or 5-nitro-2-thienyl disclosed in German Patent publications 2,161,586, 2,161,587 and 2,113, 438.

(4) The structure of a compound wherein Ra is H, Rb is cyclopropyl, E is a single bond and R is a p-(trifluoromethyl) phenyl disclosed in CAS Registry File under the codes RN=289651-68-9.

(5) an antihypertensive compound wherein Ra is a methyl, Rb is a 2-hydroxy-propyl, E is a single bond and R is a 3-pyridyl disclosed in Farmaco. Ed. Sci., 34(4), 299–310 (1979).

In order to reduce a pain such as a lumbar pain or to reduce the risk of bone fracture in a metabolic bone disease such as osteoporosis, it is required to increase the bone mass and the bone strength, and thus it is highly desired to develop a clinically useful bone-forming agent having an ability of stimulating the bone formation by osteoblasts which is considered to be surely effective.

SUMMARY OF THE INVENTION

As a result of an effort made by us for the purpose of developing a therapeutic agent having a bone formation-stimulating effect by promoting the functions of osteoblasts, the present inventors discovered that a nitrogen-containing heterocyclic compound shown below exhibits a potent bone formation-stimulating effect on the osteoblast and thus can serve as an excellent prophylactic or therapeutic agent against a metabolic bone disease, whereby establishing the invention.

Thus, the invention relates to a nitrogen-containing heterocyclic compound represented by the formula (I):

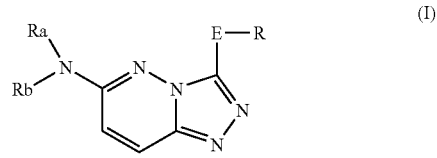

or a pharmaceutically acceptable salt thereof, wherein

Ra and Rb: the same or different and each represent H; CO-lower alkyl; $SO_2$-lower alkyl; an optionally substituted cycloalkyl; an optionally substituted aryl; or a lower alkyl which may have 1 to 3 substituents selected from the group consisting of an optionally substituted cycloalkyl, an optionally substituted aryl, an optionally substituted 4- to 8-membered monocyclic saturated or partially unsaturated heterocyclic ring, CO-lower alkyl, $SO_2$-lower alkyl, $OR^1$, $SR^1$, $NR^1R^2$, halogen, $NO_2$, CN and $COOR^1$; provided that at least one of Ra and Rb represent a group other than H; or, Ra and Rb taken together with an adjacent N atom represent a 4- to 8-membered saturated or partially unsaturated heterocyclic ring containing 1 to 2 nitrogen atoms as heteroatoms, said heterocyclic ring may be fused with a benzene ring or a cycloalkyl ring and may have A bridge and may form a spiro ring, and said heterocyclic ring may have 1 to 5 substituent, E: a single bond, $C_{1-3}$ alkylene, vinylene (—C=C—), ethynylene (—C≡C—), CO, $NR^3$, $CH_2$-J, $CONR^4$ or $NR^5CO$, J: O, S, $NR^6$, CO, SO or $SO_2$, R: an optionally substituted aryl, an optionally substituted heteroaryl, an optionally substituted cycloalkyl, an optionally substituted cycloalkenyl or an optionally substituted 4- to 8-membered monocyclic saturated or partially saturated heterocyclic ring, $R^1$ to $R^6$: the same or different and each denotes H or lower alkyl;

with the proviso that the following compounds are excluded:

(1) a compound wherein Ra and Rb taken together with an adjacent N atom represent a piperidino, E is a single bond and R is a piperidino, unsubstituted phenyl, p-(trifluoromethyl)phenyl, p-chlorophenyl or o-nitrophenyl, (2) a compound wherein Ra and Rb taken together with an adjacent N atom represent a 4-methyl-1-piperazinyl, E is a single bond, and R is an unsubstituted phenyl, p-methylphenyl, m-methylphenyl, p-methoxyphenyl, m-chlorophenyl, p-chlorophenyl or m-nitrophenyl, (3) a compound wherein R is an optionally substituted imidazolyl, 5-nitro-2-furyl or 5-nitro-2-thienyl, (4) a compound wherein Ra is H, Rb is cyclopropyl, E is a single bond and R is a p-(trifluoromethyl)phenyl, and (5) a compound wherein Ra is a methyl, Rb is a 2-hydroxypropyl, E is a single bond and R is a 3-pyridyl, and the same applies analogously to the followings.

The present invention also relates to a pharmaceutical composition comprising a nitrogen-containing heterocyclic compound represented by the formula (I) shown above or a pharmaceutically acceptable salt thereof and a pharmaceutically acceptable carrier, especially to a bone-forming agent. Furthermore, the invention encompasses use of a nitrogen-containing heterocyclic compound represented by the formula (I) or a pharmaceutically acceptable salt thereof for manufacturing a bone-forming agent for a mammalian animal as well as a method for stimulating bone formation in a mammalian animal comprising administering an effective amount of a nitrogen-containing heterocyclic compound represented by the formula (I) or a pharmaceutically acceptable salt thereof to the mammalian animal.

A compound represented by the formula (I) is detailed below.

As used herein, a "lower" means, unless otherwise specified, a straight or branched carbon chain having 1 to 6 carbon atoms. A "lower alkyl" is preferably methyl, ethyl and propyl group. In this specification, "Alk" is an abbreviation of "lower alkyl".

An "aryl" is preferably a $C_{6-14}$ monocyclic to tricyclic aryl group. More preferably, it is a phenyl or naphthyl group, particularly, a phenyl group. It is also possible that a phenyl group is fused with a $C_{5-8}$ cycloalkyl group to form, for example, an indanyl or tetrahydronaphthyl group. A "cycloalkyl" is preferably a $C_{3-14}$ cycloalkyl group, which may have bridge(s). More preferably, it is a $C_{3-10}$ cycloalkyl group, particularly, a cyclopentyl, cyclohexyl and cycloheptyl group. A "cycloalkenyl" is a group having 1 to 2 double bonds in the above-mentioned "cycloalkyl" ring.

A "4- to 8-membered monocyclic saturated or partially unsaturated heterocyclic ring" is a 4- to 8-membered monocyclic saturated heterocyclic ring having 1 to 4 heteroatoms selected from N, S and O, which may have bridge(s) and may partially have an unsaturated bond. Preferably, it is tetrahydropyranyl, tetrahydrofuranyl, pyrrolidinyl, piperidinyl, 1,2,3,6-tetrahydropyridyl, homopiperidinyl, piperazinyl, homopiperazinyl, quinucridinyl and morpholinyl group.

A "heteroaryl" is a 5- to 6-membered monocyclic heteroaryl group having 1 to 4 heteroatoms selected from N, S and O, which may be fused with a benzene ring or a 5- to 6-membered monocyclic heteroaryl to form a bi- to tri-cyclic heteroaryl group, which may be saturated partially. Such a 5- to 6-membered heteroaryl is preferably a furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidinyl, pyridazinyl, pyrazinyl and triazinyl group, while a bi- to tri-cyclic heteroaryl is preferably a benzofuranyl, benzothienyl, benzothiadiazolyl, benzothiazolyl, benzoxazolyl, benzoxadiazolyl, benzoimidazolyl, indolyl, isoindolyl, indazolyl, quinolyl, isoquinolyl, cinnolinyl, quinazolinyl, quinoxalinyl, benzodioxolyl, pyrazinopyridyl, triazolopyridyl, naphthylidinyl and imidazopyridyl group. A partially saturated heteroaryl may for example be 1,2,3,4-tetrahydroquinolyl group. More preferably, it is a pyridyl, pyrimidinyl, furyl, thienyl, thiazolyl, quinolyl, benzofuranyl, benzothienyl, indolyl, imidazopyridyl and naphthylidinyl group, especially a pyridyl group.

A substituent on an "optionally substituted aryl", and "optionally substituted heteroaryl", "optionally substituted cycloalkyl", "optionally substituted cycloalkenyl", "optionally substituted 4- to 8-membered monocyclic saturated or partially unsaturated heterocyclic ring" is preferably the same or different 1 to 5 substituents selected from Group B shown below, more preferably groups selected from Group B1, especially a halogen, OAlk and SAlk.

Group B: An Alk which may have 1 to 4 substituents selected from Group G, halogen, $NR^1R^2$, $NR^1CO$-Alk, $NO_2$, CN, $OR^1$, —O-(Alk having 1 to 4 substituents selected from Group G), $SR^1$, —S-halogeno-Alk, —O—CO-Alk, $COOR^1$, $COR^1$, $CONR^1R^2$, SoAlk, $SO_2$Alk, $SO_2NR^1R^2$, P(=O)$(OR^1)_2$, —O—$CH_2$—O—, —O—$(CH_2)_2$—O—, aryl which may have 1 to 4 substituents selected from Group D, heteroaryl which may have 1 to 4 substituents selected from Group D, —O-(aryl which may have 1 to 4 substituents selected from Group D), 4- to 8-membered monocyclic saturated or partially unsaturated-heterocyclic ring which may have 1 to 4 substituents selected from Group D, cycloalkyl and —O-cycloalkyl. In these groups, $R^1$ and $R^2$ are as defined above; "Group D" consists of Alk, halogen, halogeno-Alk, $NR^1R^2$, $NO_2$, CN, $OR^1$ and $SR^1$; "Group G" consists of halogen, $NR^1R^2$, CN, $COOR^1$, $OR^1$, $SR^1$, 4- to 8-membered monocyclic saturated or partially unsaturated heterocyclic ring which may have 1 to 4 substituents selected from Group D, aryl which may have 1 to 4 substituents selected from Group D and heteroaryl which may have 1 to 4 substituents selected from Group D; a "halogen" is I, Br, F and Cl; and a "halogeno-Alk" is a lower alkyl substituted by 1 or more halogen atoms (especially $CF_3$). The same applies analogously to the followings.

Group B1: Alk, halogen, halogeno-Alk, $NR^1R^2$, $NO_2$, CN, $OR^1$, —O-halogeno-Alk, $SR^1$, $COOR^1$, $CONR^1R^2$, $SO_2$Alk, 4- to 8-membered monocyclic saturated or partially unsaturated heterocyclic ring, phenyl and phenoxy group.

A "4- to 8-membered saturated or partially unsaturated heterocyclic ring" which may be formed from Ra and Rb taken together with an adjacent N atom may for example be a 4- to 8-membered monocyclic saturated or partially unsaturated heterocyclic ring having 1 to 2 N atoms as ring atoms with the rest of the ring atoms being C atoms. Such a heterocyclic ring may form a fused ring together with a benzene ring or a $C_{5-8}$ cycloalkyl ring, may have bridge(s), and may form a Spiro ring. Preferably, it is pyrrolydinyl, piperidinyl, homopiperidinyl, piperazinyl, pyrazolidinyl, imidazolidinyl, homopiperazinyl, perhydroazocinyl, pyrrolinyl, imidazolinyl, pyrazolinyl, 1,2,3,6-tetrahydropyridyl, 1,2-dihydropyridyl, tetrahydropyridazinyl, tetrahydropyrazinyl, 1,4,5,6-tetrahydropyrimidinyl, indolinyl, isoindolinyl, 1,2,3,4-tetrahydroquinolyl, 1,2,3,4-tetrahydroisoquinolyl, 3-azabicyclo[3.2.1]octyl, 8-azabicyclo[3.2.1]octyl, 3-azabicyclo[3.2.2]nonyl, 3-azabicyclo[3.3.1]nonyl, 7-azabicyclo[2.2.1]heptyl, isoquinucridinyl, 3-azabicyclo[3.3.2]decanyl, 3-azaspiro[5.5]undecanyl, 2-azaspiro[4.5]

decanyl, 2-azaspiro[4.4]nonyl and 8-azaspiro[4.5]decanyl and the like. It is more preferably a 4- to 8-membered monocyclic saturated or partially unsaturated heterocyclic ring which may have bridge(s), especially, pyrrolidinyl, piperidinyl, homopiperidinyl, perhydroazocinyl, 1,2,3,6-tetrahydropyridyl, 3-azabicyclo[3.2.1]octyl, 8-azabicyclo[3.2.1]octyl, 3-azabicyclo[3.2.2]nonyl and 3-azabicyclo[3.3.1]nonyl group. A piperidyl group is especially preferred.

Such a heterocyclic ring may have substituent(s), and such a substituent is preferably 1 to 5 substituents selected from Group B listed above. More preferably, it is 1 to 5 substituents selected from (Alk which may have substituent(s) selected from COOR$^1$, OR$^1$ and phenyl), halogen, NR$^1$R$^2$, CN, OR$^1$, —O-(Alk which may have substituent(s) selected from COOR$^1$, OR and phenyl), SR$^1$, COOR$^1$, CONR$^1$R$^2$ and phenyl, especially 1 to 2 substituents selected from Alk, halogen, OR$^1$ and COOR$^1$.

Among the invention compounds (I), those preferred are listed below.

(1) A compound wherein —NRaRb forms a 4- to 8-membered saturated or partially unsaturated heterocyclic ring having 1 to 2 N atoms as heteroatoms which may be fused with a benzene ring or a cycloalkyl ring, which may have bridge(s), or which may form spiro ring(s) and which may have 1 to 5 substituents selected from Group B; E is a single bond, C$_{1-3}$ alkylene, vinylene, ethynylene, CONH, CH$_2$NH, CH$_2$O or CH$_2$S; R is aryl which may have 1 to 5 substituents selected from Group B or heteroaryl which may have 1 to 5 substituents selected from Group B.

(2) A compound wherein E is a single bond, C$_{1-3}$ alkylene, vinylene or ethynylene; R is an aryl having 1 to 5 substituents selected from Group B1 or heteroaryl having 1 to 5 substituents selected from Group B1.

(3) A compound wherein —NRaRb is a 4- to 8-membered monocyclic saturated or partially unsaturated heterocyclic ring which may have one N atom as a ring heteroatom and may have a bridge, and may have 1 to 2 substituents selected from Alk, halogen, OR$^1$ and COOR$^1$; E is a single bond; R is a phenyl having, at its m-position, a substituent selected from a halogen, OAlk and SAlk or a pyridyl having, at its 6-position, a substituent selected from a halogen, OAlk and SAlk.

An especially preferred compound in the invention is nitrogen-containing heterocyclic compounds listed below and their pharmaceutically acceptable salts.

6-Azocan-1-yl-3-(6-methoxypyridin-2-yl)-1,2,4-triazolo[4,3-b]pyridazine, 6-azepan-1-yl-3-(6-bromopyridin-2-yl)-1,2,4-triazolo[4,3-b]pyridazine, 3-(3-methoxyphenyl)-6-(piperidin-1-yl)-1,2,4-triazolo[4,3-b]pyridazine, 3-(3-bromophenyl)-6-(piperidin-1-yl)-1,2,4-triazolo[4,3-b]pyridazine, 6-azepan-1-yl-3-(6-methoxypyridin-2-yl)-1,2,4-triazolo[4,3-b]pyridazine, 6-(4-fluoropiperidin-1-yl)-3-(6-methoxypyridin-2-yl)-1,2,4-triazolo[4,3-b]pyridazine, 6-(3-azabicyclo[3.2.1]octan-3-yl)-3-(6-methoxypyridin-2-yl)-1,2,4-triazolo[4,3-b]pyridazine, 6-(4,4-difluoropiperidin-1-yl)-3-(6-methoxypyridin-2-yl)-1,2,4-triazolo[4,3-b]pyridazine, 6-(3,3-difluoropiperidin-1-yl)-3-(6-methoxypyridin-2-yl)-1,2,4-triazolo [4,3-b]pyridazine, 6-azocan-1-yl-3-(6-bromopyridin-2-yl)-1,2,4-triazolo[4,3-b]pyridazine, and 6-(8-azabicyclo[3.2.1]octan-8-yl)-3-(6-bromopyridin-2-yl)-1,2,4-triazolo[4,3-b]pyridazine.

Some of the invention substituents may allow geometric isomers or tautomers to exist, and the invention encompasses all these isomers as being separated or in a mixture. An invention compound may have an asymmetric carbon atom, based on which an optical isomer may exist. The invention encompasses all of these optical isomers as mixtures or individually separated forms.

An invention compound (I) may form an acid addition salt or a salt with a base depending on the type of the substituent. Such a salt is a pharmaceutically acceptable salt, preferably an acid addition salt with an inorganic acid such as hydrochloric acid, hydrobromic acid, hydroiodic acid, sulfuric acid, nitric acid, phosphoric acid and the like and with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, glutamic acid and the like, a salt with an inorganic base including a metal such as sodium, potassium, magnesium, calcium, aluminum and the like, and with an organic base such as methylamine, ethylamine, ethanolamine, lysine, ornithine and the like, as well as an ammonium salt.

Furthermore, the invention includes various hydrates or solvates of an invention compound (I) or its salt, as well as the forms of polymorphic crystals.

(Production Methods)

A representative method for producing an invention compound (I) is described below.

An invention compound and a pharmaceutically acceptable salt thereof can be produced by utilizing the characteristics based on its skeleton and the types of the substituents and applying various known synthetic methods. In such a case, it is advantageous sometimes from a manufacturing technological point of view that a certain functional group in a starting material or an intermediate is substituted by a suitable protective group, i.e., a group which can readily be converted back to this certain functional group. Thereafter, the protective group is removed if necessary to obtain an intended compound. Such a functional group may for example be a hydroxyl group or carboxyl group, and its protective group may be those listed for example in Greene and Wuts, Protective Groups in Organic Synthesis, 2nd Ed., and can be used appropriately depending on the reaction conditions.

A representative method for producing an invention compound is described below.

1st Preparation Method

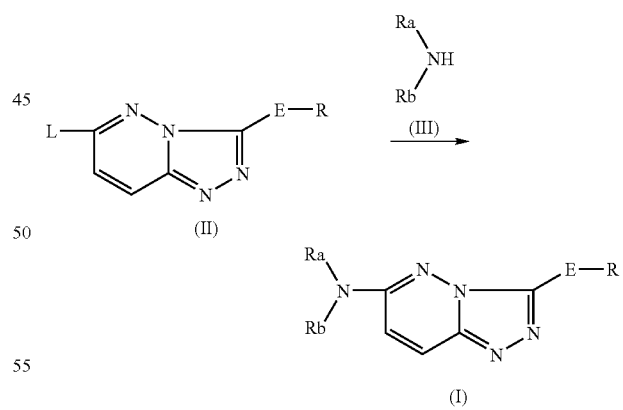

wherein L is a leaving group such as a halogen atom or an organic sulfonate the same applies analogously to the followings.

An invention compound (I) can be obtained by a standard N-alkylation method, for example by reacting an amine derivative (III) and a compound (II) having an ordinary leaving group such as a halogen atom or an organic sulfonate in the presence or absence of a base such as potassium carbonate, triethylamine, sodium hydride and the like, in an inert solvent such as N,N-dimethylformamide (DMF), toluene, tetrahydrofuran (THF), acetonitrile and the like or without using any solvent with cooling or under reflux.

Other Preparation Method

A compound obtained in the first preparation method described above can further be subjected to a standard substituent-modifying reaction, for example, reduction from a nitro group to an amino group, amidation, sulfonamidation, N-alkylation, esterification, ester hydrolysis, hydroxyl group etherification, thioether sulfonation, halogenation, olefin-derivatization, and the like to obtain an invention compound having a desired substituent. Any of these reactions can readily be conducted in accordance with a method described for example in ORGANIC FUNCTIONAL GROUP PREPARATIONS Second Edition (Sandler, Karo).

(Method for Preparing Starting Material)

Preparation Method A

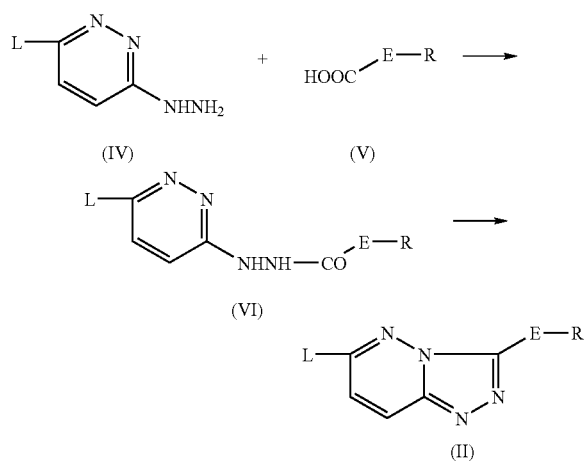

The starting material (II) of the present application can be prepared by subjecting a hydrazine compound (IV) and a carboxylic acid compound (V) to a dehydration condensation reaction to form a hydrazide compound (VI) followed by a cyclization.

The dehydration condensation reaction in the first step can be conducted by a standard method, for example by using a free carboxylic acid and a coupling agent such as 1-(3-dimethylaminopropyl)-3-ethylcarbodiimide (WSCD) or a carboxylic acid-activating agent such as 1,1'-carbonyldiimidazole, or using a reactive derivative of a carboxylic acid (for example, acid halide such as acid chloride and acid bromide; acid azides; active esters prepared from methanol, ethanol, benzyl alcohol, optionally substituted phenol, N-hydroxysuccinimide and the like; symmetric acid anhydrides; mixed acid anhydrides with alkylcarbonates, p-toluenesulfonic acid and the like).

The reaction is conducted using equimolar amounts or an excessive amount of any one of the reactants, in an organic solvent which is inert to the reaction, such as pyridine, THF, methylene chloride, DMF, acetonitrile and the like. The reaction temperature is selected appropriately depending on the type of the reactive derivative. In a case of a certain reactive derivative, it may be advantageous to add a base such as 4-dimetylaminopyridine for promoting the reaction.

The cyclization in the second step can be conducted by a reaction in the presence or absence of an acid such as acetic acid, p-toluenesulfonic acid, hydrochloric acid and the like, in a solvent such as xylene, ethylene glycol and the like, or without using any solvent. This reaction can be conducted at room temperature or with heating under reflux.

Preparation Method B

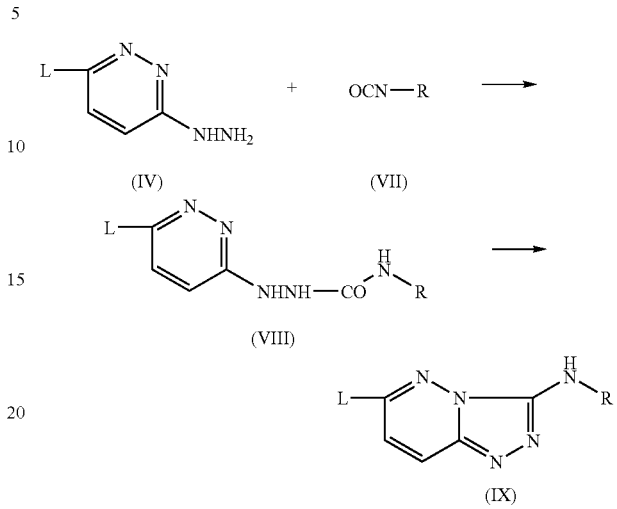

An starting material (IX) of the present application can be produced by coupling a compound (IV) with an isocyanate compound (VII) in a solvent inert to the reaction such as acetonitrile to form a compound (VIII) followed by adding 1,2-dibromo-1,1,2,2-tetrachloroethane and triphenylphosphine in the presence of a base such as triethylamine whereby effecting a cyclization. The reaction can be conducted appropriately by a standard method at room temperature or with heating under reflux.

A reaction product obtained by each preparation method described above can be isolated and purified as a free base, free acid, its salt, hydrate or any of various solvates. A salt can be produced by an ordinary salt formation reaction. The isolation and the purification can be conducted by applying ordinary chemical procedures such as extraction, concentration, distillation, crystallization, filtration, recrystallization, various chromatographies and the like. Each isomer can be isolated utilizing a physicochemical difference between isomers. For example, an optical isomer can be separated by an ordinary optical resolution method, for example, fractional crystallization or chromatography. An optical isomer can be synthesized from a suitable optically active starting compound.

INDUSTRIAL APPLICABILITY

An invention compound has an ability of stimulating the bone formation by osteoblasts, and is useful in preventing or treating a metabolic bone disease associated with a lower bone formation ability relative to the bone resorption ability. Such a metabolic bone disease includes osteoporosis, osteitis fibrosa (hyperparathyroidism), osteomalacia and Paget's disease which affects the parameters of systemic bone metabolism. It is useful especially in a senile osteoporosis associated with a reduced bone formation ability.

An invention bone-forming agent may also be useful in promoting a cure from a bone disease in the field of orthopedics such as bone fracture, bone loss and osteoarthritis, as well as in the field of dentistry for treating a periodontitis or stabilizing an artificial dental root.

A phenotypic trait of osteoblasts includes an alkaline phosphatase (ALP) activity, production of bone matrix proteins (collagen, osteocalcin, osteonectin, osteopontin and the like), presence of an active vitamin D3 receptor, parathyroid hormone receptor, estrogen receptor, androgen receptor (Molecular Medicine, Vol. 30, No. 10, 1232 (1993)). The ALP is increased at an early stage of the onset of the osteoblast functions (Journal of Cellular Physiology, Vol. 143, 420 (1990)). The role of the ALP for the bone formation by the osteoblast is believed to be to increase the phosphate ion level at a site of the bone formation and to decompose pyrophosphoric acid which is an! inhibitor of calcification ("SAIBO KOGAKU", Vol. 13, No. 12, 1062 (1994)). It was also reported that a subcutaneous implantation of the ALP bound covalently to a collagen sheet caused the calcification (J. Clin. Invest., 89, 1974 (1992)). Accordingly, the osteoblast-induced ALP activity elevation can be regarded as an index of the bone formation.

BEST MODE FOR CARRYING OUT THE INVENTION

The tests for exhibiting the pharmacological effects of invention compounds are described below together with their results.

Experimental Example 1

Alkaline Phosphatase (ALP) Activity Measurement in Mouse Osteoblast Cell Line

A mouse osteoblast cell line MC3T3-E1 was seeded at the density of 3000 cells/well in 96-well plates in 5% fetal bovine serum (FBS)-supplemented α-minimum essential medium (MEM) and incubated for 4 to 6 hours. To the cell thus cultured, a test compound dissolved in dimethyl sulfoxide (DMSO) (final concentration of DMSO: 0.5%) was added, and the incubation was continued for further 3 days. After washing the cells with a phosphate-buffered physiological saline, the substrate was added and incubated at 37° C. for 10 to 15 minutes. The reaction was stopped by adding 0.5M sodium hydroxide, and the absorbance at a wavelength of 405 nm (correction wavelength: 492 nm) was measured and represented by a % value based on the value in the control group being regarded as 100%, from which the ALP activity was calculated. The measurement described above was in accordance with the method by Lowry et al (Journal of Biological Chemistry, Vol. 207, page 19, (1954)).

The invention compounds of Examples 2, 8, 12, 21, 23, 24, 27, 28, 33, 34, 35, 38, 39, 42, 45, 54, 65, 67, 72, 75, 76, 81, 84, 85, 86, 87, 92, 93, 94, 95, 96, 100, 103, 107, 114, 116, 117 and 118 exhibited the ALP activities of 300% or higher at 300 nM when compared with the control group.

Experimental Example 2

Bone Formation Stimulation Test of Rat Topical Administration

Figure 1:
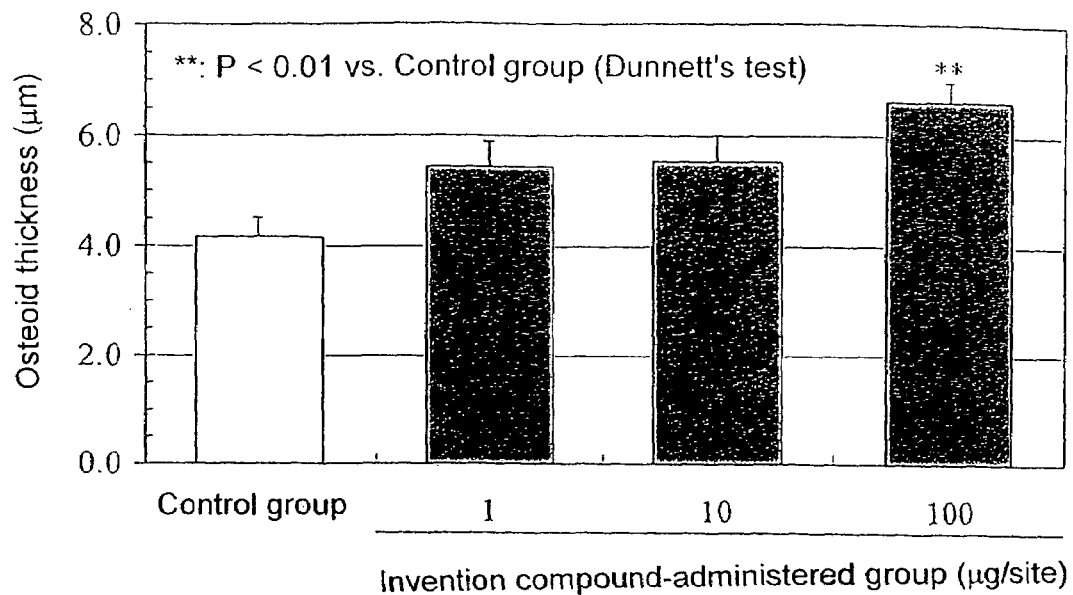
FIG. 1 shows the osteoid thickness in an invention compound treatment group and a control group in Experimental Example 2.
Figure 2:
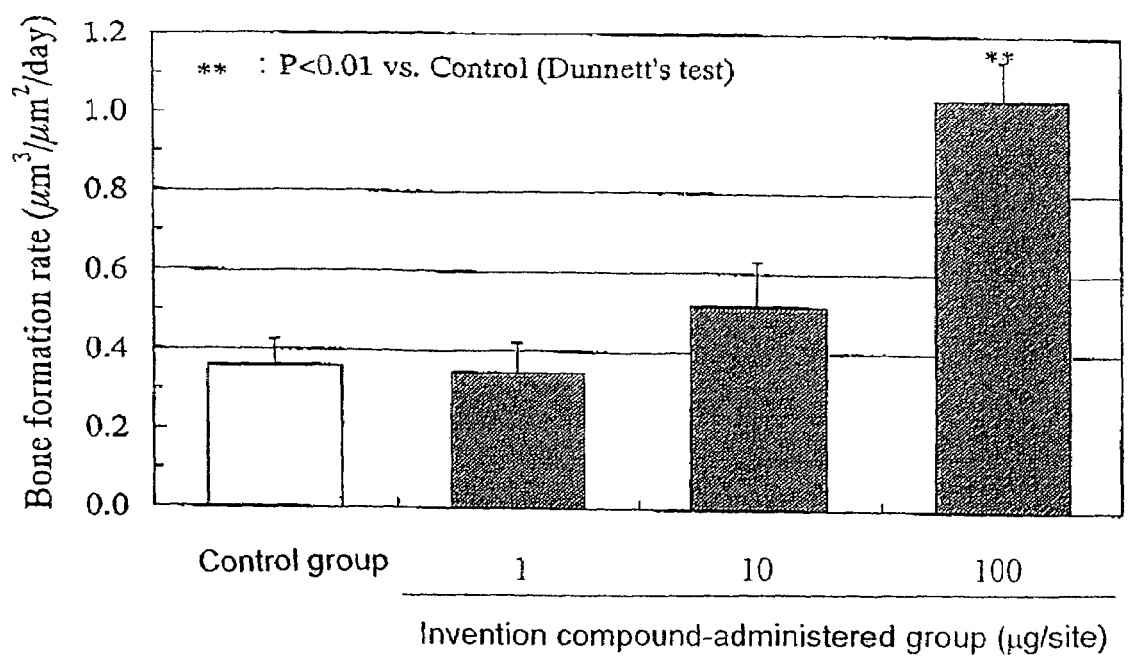
FIG. 2 shows the bone formation rate in an invention compound treatment group and a control group in Experimental Example 2.

The compound of Example 23 according to the present invention (1, 10 or 100 μg) was dispersed in 0.1 ml of a mineral oil and given successively for 10 days once a day using a 1 ml syringe fitted with a 25 G injection needle subcutaneously to the right temporal region of each of 10-week old male Wistar rats (n=6) under anesthesia with ether. In a control group, each rat was treated only with 0.1 ml of the mineral oil once a day for successive 10 days. On the 11th day of the treatment, the drug was discontinued and on the 18th day each rat was sacrificed to remove the calvaria. Before sacrificing the animal, tetracyclin (25 mg/kg) was given on the 10th day of the treatment and then calcein (20 mg/kg) was given subcutaneously to the dorsal area on the 16th day for labeling the bone. The calvaria thus obtained was fixed in 70% ethanol, and coronal sections were made according to a standard procedure and subjected to a bone morphometric measurements. Osteoids thickness and bone formation rate in an invention compound treatment group and a control group are shown in FIG. 1 and FIG. 2.

As a result of the administration of the invention compounds, significant increases in osteoid thickness and bone formation rate were observed, exhibiting excellent bone formation-stimulating effects of the invention compounds.

A pharmaceutical composition containing an invention compound (I) or pharmaceutically acceptable salt thereof and a pharmaceutically acceptable carrier can be prepared by an ordinary method using one or more of a compound represented by the formula (I) or pharmaceutically acceptable salt thereof together with a pharmaceutical carrier, excipient and other additives employed usually in a formulation. The administration can be conducted in various dosage forms orally as a tablet, pill, capsule, granule, powder, liquid, inhalation formulation and the like, or parenterally as an injection formulation such as an intravenous injection, intramuscular injection and the like, as well as a suppositories, percutaneous liquid formulations, ointments, percutaneous patches and the like.

A solid composition for an invention oral administration may be a tablet, powder, granule and the like. In such a solid composition, one or more active substance is mixed with at least one inert diluent such as lactose, mannitol, glucose, hydroxypropyl cellulose, microcrystalline cellulose, starch, polyvinylpyrrolidone, magnesium aluminate metasilicate and the like. The composition may contain additives other than the inert diluent as customary in the art, including a lubricant such as magnesium stearate, a disintegrant such as calcium fibrinoglycolate, a stabilizer, a dissolution aid such as glutamic acid or aspartic acid. A tablet or pill may be sugar-coated if necessary with sucrose, gelatin, hydroxypropyl cellulose, hydroxypropylmethyl cellulose phthalate and the like or covered with a gastric or enteric film coating.

A liquid composition for an oral administration contains a pharmaceutically acceptable emulsifier, solubilizer, suspending agent, syrup, elixir and the like, together with an ordinarily employed inert diluent such as a purified water and ethanol. Such a composition may contain, in addition to an inert diluent, other auxiliary agents such as a humectant, suspending agent, as well as a sweetener, flavor, fragrance and preservative.

An injection formulation for a parenteral administration includes an aseptic aqueous or non-aqueous solution, suspension and emulsion. Such an aqueous solution and suspension may contain a distilled water for injection or a physiological saline. A non-aqueous solution and suspension may contain propylene glycol, polyethylene glycol, a vegetable oil such as an olive oil, an alcohol such as ethanol, as well as Polysorbate 80 (trade name) and the like. Such a composition may also contain auxiliary agents such as a preservative, humectant, emulsifier, dispersing agent, dissolution aid (for example, glutamic acid, aspartic acid) and the like. Any of these materials can be made aseptic by filtration through a filter retaining bacteria, incorporation of a sterilizing agent or irradiation. Any of these material can be formulated as an aseptic solid composition which is to be reconstituted just before use with an aseptic water or aseptic solvent for injection.

In a usual oral administration, the daily dose is about 0.001 to 10 mg/kg body weight, preferably 0.01 to 5 mg/kg, which may be given at once, or twice to four times in portions. When given intravenously, the daily dose is about 0.0001 to 1 mg/kg body weight, which may be given at once, or several times in portions. The dosage may vary depending on the symptom, age, sex and the like of each individual patient.

EXAMPLES

The invention is further described in the following Examples, which are not intended to restrict the invention compositions. The Reference Examples indicate methods for producing starting materials. Abbreviations in the text are Dat: physicochemical characteristics, F: FAB-MS (M+H)$^+$; other symbols are as defined above.

Reference Example 1

A mixture of (6-chloropyridazin-3-yl)hydrazine, 4-nitrobenzoic acid, WSCD hydrochloride and THF was stirred at room temperature for 2 hours. The reaction solution was combined with water, and the precipitate was collected by filtration, washed with water and diethyl ether to obtain N'-(6-chloropyridazin-3-yl)-4-nitrobenzohydrazide. To this, acetic acid was added, and the mixture was stirred at 110° C. for 2 hours, the reaction solution was concentrated under reduced pressure, and the resultant crude crystal was washed with ethanol to obtain 6-chloro-3-(4-nitrophenyl)-1,2,4-triazolo[4,3-b]pyridazine. Dat (F:276).

Reference Example 2

To a solution of (6-chloropyridazin-3-yl)hydrazine and triethylamine in THF, 3-cyanobenzoyl chloride was added with cooling in ice, and stirred at room temperature for 1 hour. The reaction solution was combined with water, and the precipitate was collected by filtration, washed with water and diethyl ether to obtain, N'-(6-chloropyridazin-3-yl)-3-cytanobenzohydrazide. To this, acetic acid was added, and the mixture was stirred at 110° C. for 2 hours, the reaction solution was concentrated under reduced pressure, and the resultant crude crystal was washed with ethanol to obtain 3-(6-chloro-1,2,4-triazolo[4,3-b]pyridazin-3-yl)benzonitrile. Dat (F:256).

Reference Example 3

A mixture of (6-chloropyridazin-3-yl)hydrazine, 3-dimethylaminobenzoic acid, WSCD hydrochloride and THF was stirred at room temperature for 2 hours. The reaction solution was combined with water, and the precipitate was collected by filtration, washed with water and isopropyl ether to obtain N'-(6-chloropyridazin-3-yl)-3-dimethylaminobenzohydrazide. To this, ethylene glycol was added and the mixture was stirred at 160° C. for 4 hours. After allowing to cool to room temperature, followed by purification by a standard method, 6-chloro-3-(3-dimethylaminophenyl)-1,2,4-triazolo[4,3-b]pyridazine was obtained. Dat (F:274).

Reference Example 4

A solution of 3-methoxyphenyl isocyanate and 3-chloro-6-hydrazinopyridazine in acetonitrile was stirred at room temperature for 30 minutes, and 1,2-dibromo-1,1,2,2-tetrachloroethane was added and the mixture was stirred at room temperature for further 2 hours. This reaction solution was combined with triethylamine and triphenylphosphine with cooling in ice, and stirred at room temperature for 3 days. Then, the reaction solution was concentrated under reduced pressure, purified by a standard method to obtain 6-chloro-N-(3-methoxyphenyl)-1,2,4-triazolo[4,3-b]pyridazin-3-amine. Dat (F:276).

Similarly to Reference Example 1, the compounds of Reference Examples 5 to 50 indicated in Tables 1 to 2 shown below were obtained.

Example 1

A mixture of 3-(6-chloro-1,2,4-triazolo[4,3-b]pyridazin-3-yl)benzonitrile (450 mg) and piperidine (5 ml) was stirred with heating under reflux for 2 hours. The reaction solution was concentrated under reduced pressure, and the resultant residue was extracted with chloroform. The extract was washed with saturated aqueous solution of ammonium chloride and brine, dried over anhydrous magnesium sulfate, and concentrated under reduced pressure. The resultant crude crystals were recrystallized from ethanol to obtain 3-[6-(piperidin-1-yl)-1,2,4-triazolo[4,3-b]pyridazin-3-yl)benzonitrile (435 mg) as slightly yellowish crystals.

Example 2

To a solution of N-cyclopentyl-3-(3-methoxyphenyl)-1,2,4-triazolo[4,3-b]pyridazine-6-amine (300 mg) in DMF (5 ml), 60% sodium hydride (44 mg) was added with cooling in ice, and the mixture was stirred at an ice-cooling temperature to room temperature for 1 hour, combined with methyl iodide (68 μl), and stirred further for 2 hours. The reaction mixture was combined with water, and extracted with ethyl acetate. The extract was washed with brine and dried over anhydrous magnesium sulfate, and then concentrated under reduced pressure. The resultant residue was purified by silica gel column chromatography (eluent: chloroform:methanol=20:1), recrystallized from ethyl acetate to obtain N-cyclopentyl-3-(3-methoxyphenyl)-N-methyl-1,2,4-triazoro[4,3-b]pyridazine-6-amine (145 mg) as pale yellow crystals.

Example 3

To a mixture of potassium hydroxide (98 mg) and DMSO (5 ml), 6-azepan-1-yl-3-(1H-indol-2-yl)-1,2,4-triazolo[4,3-b]pyridazine (501 mg) was added, and the mixture was stirred at room temperature for 30 minutes, and then combined with methyl iodide (0.15 ml) and then stirred for further 2 hours at room temperature. The reaction mixture was combined with water, and the resultant solids were collected by filtration, washed with a solvent a mixture of water and methanol, and then purified by silica gel column chromatography (eluent: chloroform: methanol=99:1). The resultant crude crystals were recrystallized from ethanol to obtain 6-azepan-1-yl-3-(1-methylindol-2-yl)-1,2,4-triazolo[4,3-b]pyridazine (40 mg) as colorless crystals.

Example 4

A mixture of 3-[6-(piperidin-1-yl)-1,2,4-triazolo[4,3-b]pyridazine-3-yl]aniline (180 mg) and acetic anhydride (3 ml) was stirred at room temperature for 6 hours. The reaction solution was concentrated under reduced pressure, and the resultant crude crystals were washed with diethyl ether to obtain 3'-[6-(piperidin-1-yl)-1,2,4-triazolo[4,3-b]pyridazin-3-yl]acetoanilide (190 mg) as colorless crystals.

Example 5

To a solution mixture of 6-piperidin-1-yl-3-piperidin-3-yl-1,2,4-triazolo[4,3-b]pyridazine (670 mg), triethylamine (360 mg) and methylene chloride (15 ml), methanesulfonyl chloride (320 mg) was added and the mixture was stirred at room temperature for 8 hours. The reaction solution was concentrated under reduced pressure, and the resultant residue was extracted with ethyl acetate. The extract was washed successively with water and brine, dried over anhydrous magnesium sulfate, and concentrated under reduced pressure. The resultant crude crystals were recrystallized from ethanol to obtain 3-(1-methanesulfonylpiperidin-3-yl)-6-piperidin-1-yl-1,2,4-triazolo[4,3-b]pyridazine (230 mg) as colorless crystals.

Example 8

A mixture of 6-azocan-1-yl-3-(6-chloropyridin-2-yl)-1,2,4-triazolo[4,3-b]pyridazine (360 mg), sodium methoxide (570 mg) and toluene (20 ml) was stirred with heating under reflux for 3 hours. After allowing to cool to room temperature, the reaction solution was concentrated under reduced pressure, and the resultant residue was extracted with ethyl acetate. The extract was washed with water and brine, dried over anhydrous magnesium sulfate, and concentrated under reduced pressure. The resultant crude crystal was washed with diethyl ether to obtain 6-azocan-1-yl-3-(6-methoxypyridin-2-yl)-1,2,4-triazolo[4,3-b]pyridazine (290 mg) as pale yellow crystals.

Example 9

To a solution mixture of 3-[6-(piperidin-1-yl)-1,2,4-triazolo[4,3-b]pyridazine-3-yl]benzoic acid (430 mg), a catalytic amount of DMF and THF (10 ml), oxalyl chloride (0.44 ml) was added with cooling in ice, and the mixture was stirred at room temperature for 2 hours and then ammonia gas was passed with cooling in ice for 15 minutes. The reaction solution was concentrated under reduced pressure, and the resultant residue was combined with chloroform:methanol (10:1), and then insoluble materials were filtered off. The filtrate was concentrated under reduced pressure, and the resultant crude crystals were recrystallized from ethanol to obtain 3-[6-(piperidin-1-yl)-1,2,4-triazolo[4,3-b]pyridazin-3-yl]benzamide (242 mg) as slightly tan crystals.

Example 10

To a solution of 3-[3-(methylsulfanyl)phenyl]-6-piperidin-1-yl-1,2,4-triazolo[4,3-b]pyridazine (550 mg) in methylene chloride (30 ml), 3-chloroperbenzoic acid (1.25 g) was added at room temperature, and the mixture was stirred for 13 hours. The reaction solution was combined with water, and diluted with methylene chloride. The organic phase washed successively with water, 1M aqueous solution of sodium hydroxide and brine, dried over anhydrous sodium sulfate, and concentrated under reduced pressure. The resultant residue was purified by silica gel column chromatography (eluent:chloroform:methanol=98:2) and washed with ethanol to obtain 3-[3-(methylsulfonyl)phenyl]-6-piperidin-1-yl-1,2,4-triazolo[4,3-b]pyridazine (250 mg) as colorless crystals.

Example 11

A solution mixture of concentrated sulfuric acid (1.5 ml) and water (3 ml) was cooled to −5° C., and 4-(6-piperidin-1-yl-1,2,4-triazolo[4,3-b]pyridazin-3-yl)-1,3-thiazol-2-amine (0.90 g), copper (II) sulfate (1.50 g) and sodium bromide (0.62 g) were added successively, and the mixture was stirred at 0° C. for 5 minutes. Then, a solution of sodium nitrite (0.25 g) in water (1.6 ml), followed by stirring at room temperature overnight. The reaction solution was combined with water, chloroform and 2-propanol, and insoluble materials were filtered off. The resultant organic phase was washed with water, dried over anhydrous magnesium sulfate, and concentrated under reduced pressure. The resultant residue was purified by silica gel column chromatography (eluent: chloroform:methanol=20:1) to obtain crude crystals, which were then recrystallized from ethanol-diethyl ether to obtain 3-(2-bromo-1,3-thiazol-4-yl)-6-piperidin-1-yl-1,2,4-triazolo[4,3-b]pyridazine (75 mg) as pale yellow crystals.

Example 12

A mixture of 6-(6-azepan-1-yl-1,2,4-triazolo[4,3-b]pyridazin-3-yl)pyridine-2-ol (700 mg) and phosphorus tribromide (7 ml) was stirred at 130° C. for 6 hours. After allowing to cool to room temperature, an ice-water was added, and the mixture was neutralized with saturated aqueous solution of potassium carbonate, and extracted with chloroform. The extract was washed with saturated aqueous solution of sodium hydrogen carbonate and brine, dried over anhydrous sodium sulfate, and then concentrated under reduced pressure. The resultant residue was purified by silica gel column chromatography (eluent: chloroform:methanol=98:2) and recrystallized from ethanol to obtain 6-azepan-1-yl-3-(6-bromopyridin-2-yl)-1,2,4-triazolo[4,3-b]pyridazine (240 mg) as colorless crystals.

Example 13

To a solution of diethyl [(6-azepan-1-yl-1,2,4-triazolo[4,3-b]pyridazin-3-yl)methyl]phosphonate (367 mg) in THF (10 ml), potassium tert-butoxide (127 mg) was added with cooling in an ice bath, and the mixture was stirred at room temperature for 40 minutes. The resultant red solution was combined with 2-bromobenzaldehyde (0.128 ml), and stirred at room temperature for further 1 hour. The reaction solution was combined with water, and extracted with ethyl acetate. The extract was washed with water and brine, dried over anhydrous magnesium sulfate, and concentrated under reduced pressure. The resultant white solids were recrystallized from methanol to obtain 6-azepan-1-yl-3-[(E)-2-(2-bromophenyl)vinyl]-1,2,4-triazolo[4,3-b]pyridazine (152 mg) as colorless crystals.

Example 14

A mixture of ethyl 6-chloro-1,2,4-triazolo[4,3-b]pyridazine-3-carboxylate (3.00 g) and hexamethylenimine (10 ml) was stirred at 100° C. for 2 hours. The reaction solution was concentrated under reduced pressure, and the resultant residue was purified by silica gel column chromatography (eluent: chloroform:methanol=30:1) to obtain crude crystals which were then recrystallized from ethanol and diethyl ether to obtain 3-(azepan-1-ylcarbonyl)-6-azepan-1-yl-1,2,4-triazolo[4,3-b]pyridazine (0.23 g) as colorless crystals.

Example 15

A mixture of 1-[(benzyloxy)carbonyl]piperidine-3-carboxylic acid (2.44 g), 3-chloro-6-hydrazinopyridazine (1.34 g), WSCD hydrochloride (2.13 g) and methylene chloride (60 ml) was stirred at room temperature for 16 hours. The reaction solution was concentrated under reduced pressure and extracted with ethyl acetate. The extract was washed successively with water and brine, dried over anhydrous sodium sulfate, and concentrated under reduced pressure. The resultant reside was combined with acetic acid (80 ml), stirred at 100° C. for 2 days, and then the solvent was distilled off under reduced pressure. The resultant crude crystals were washed with ethanol, and stirred with heating under reflux in piperidine (10 ml) for 3 hours. The reaction solution was concentrated under reduced pressure, and purified by silica gel column chromatography (eluent: chloroform:methanol=97:3). The resultant colorless solids were combined with ethanol (40 ml) and 10% palladium-carbon (150 mg), and stirred under hydrogen atmosphere at room temperature for 6 hours, and then the catalyst was filtered off. The resultant filtrate was concentrated under reduced pressure to obtain 6-piperidin-1-yl-3-piperidin-3-yl-1,2,4-triazolo[4,3-b]pyridazine (1.18 g) as a colorless amorphous.

Example 16

To a solution of ethyl 2-aminothiazole-4-carboxylate (4.56 g) in THF (200 ml), 1M aqueous solution of sodium hydroxide (30 ml) was added and the mixture was stirred at room temperature for 3 hours. The reaction solution was combined with 1M hydrochloric acid (30 ml), concentrated, and the resultant residue was dissolved in DMF (50 ml). Then, 6-chloropyridazin-3-ylhydrazine (3.83 g) and WSCD hydrochloride (6.09 g) were added, and the mixture was stirred at room temperature. The reaction solution was combined with water, and the precipitate was collected by filtration, and washed with water and diethyl ether, combined with acetic acid (30 ml), heated under reflux, and then the reaction solution was concentrated under reduced pressure. The residue was combined with saturated aqueous solution of sodium hydrogen carbonate, and extracted with ethyl acetate. The organic layer was washed with water and brine, dried over anhydrous magnesium sulfate, and concentrated under reduced pressure. To this, piperidine (10 ml) was added and the mixture was heated at 100° C., and the reaction solution was concentrated under reduced pressure, and the resultant residue was purified by silica gel column chromatography (eluent: chloroform:methanol=30:1) to obtain 3-(2-aminothiazol-4-yl)-6-(piperidin-1-yl)-1,2,4-triazolo[4,3-b]pyridazine (0.92 g) as yellow solids.

Example 17

To a solution of 6-hydrazino-N-methyl-N-phenylpyridazine-3-amine (1.14 g) in methylene chloride (10 ml), 6-chloropicolic acid (0.83 g) and WSCD hydrochloride (1.22 g) were added, and the mixture was stirred at room temperature overnight. The reaction solution was purified by silica gel column chromatography (eluent: chloroform) to obtain 6-chloro-N'-{6-[methyl(phenyl)amino]pyridazin-3-yl}pyridine-2-carbohydrazide (0.57 g). This compound (0.56 g) was stirred at 150° C. overnight in xylene (20 ml), and the reaction solution was concentrated to obtain 3-(chloropyridin-2-yl)-N-methyl-N-phenyl-1,2,4-triazolo[4,3-b]pyridazine-6-amine (0.54 g) as colorless solids.

Example 18

A mixture of 6-chloro-3-(6-chloropyridin-2-yl)-1,2,4-triazolo[4,3-b]pyridazine (620 mg), heptamethylenimine (1.32 g) and 1,4-dioxane (20 ml) was stirred at 100° C. for 9 hours. After allowing to cool to room temperature, the reaction solution was concentrated under reduced pressure, and the resultant residue was extracted with ethyl acetate. The extract was washed successively with 5% aqueous solution of citric acid, water, saturated aqueous solution of sodium hydrogen carbonate and brine, dried over anhydrous sodium sulfate, and concentrated under reduced pressure. The resultant crude crystal was recrystallized from ethanol, to obtain 6-azocan-1-yl -3-(6-chloropyridin-2-yl)-1,2,4-triazolo[4,3-b]pyridazine (370 mg) as grayish white crystals.

Example 19

A mixture of 6-(6-chloro-1,2,4-triazolo[4,3-b]pyridazin-3-yl)pyridin-2-ol (960 mg) and piperidine (10 ml) was stirred at 100° C. for 3 hours. After allowing to cool to room temperature, the reaction solution was concentrated under reduced pressure, and the resultant crystalline residue was recrystallized from ethanol to obtain 6-(6-piperidin-1-yl-1,2,4-triazolo[4,3-b]pyridazin-3-yl) pyridin-2-ol (820 mg) as grayish white crystals.

By proceeding similarly to Example 1 optionally with conducting an ordinary salt formation using 4M hydrogen chloride—ethyl acetate, the compounds of Examples 20 to 170 were obtained. The compound of Example 108 was obtained similarly to Example 2, the compound of Example 109 similarly to Example 3, the compounds of Examples 110 and 111 similarly to Example 4, the compounds of Examples 112 to 114 similarly to Example 8, the compound of Example 115 similarly to Example 10, the compounds of Examples 116 to 118 similarly to Example 12, the compounds of Examples 119 and 120 similarly to Example 13, the compound of Example 121 similarly to Example 18, and the compounds of Example 122 to 123 similarly to Example 19.

The structures and the physicochemical characteristics of the compounds of Reference Examples are indicated in Tables 1 to 2 shown below, and the structures and the physicochemical characteristics of the compounds of Examples are indicated in Tables 3 to 11. The compounds indicated in Table 12 can readily be produced using appropriate starting materials almost similarly to the methods described in Examples or Preparation Method described above, with or without any modification obvious to those skilled in the art.

The abbreviations in Tables are Rex: Reference Example number; Ex: Example number; Dat: physicochemical characteristics (F: FAB-MS (M+H)$^+$; M: melting point [° C.]; (d): decomposition; N1: NMR (DMSO-d$_6$, TMS internal standard) characteristic peak δ ppm); Sal: salt (void: free base; HCl: hydrochloride; 2HCl: dihydrochloride); Me: methyl; Et: ethyl; and Ac: acetyl.

TABLE 1

| Rex | —E—R | Dat |
|---|---|---|
| 5 | 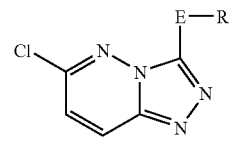 | F: 261 |
| 6 | 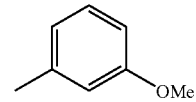 | N1: 3.93(3H, s), 7.60(1 H, d, J=9.7Hz), 8.93(1 H, t, J=1.8Hz) |
| 7 | 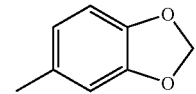 | F: 275 |

TABLE 1-continued
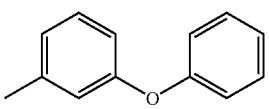
| Rex | —E—R | Dat |
|---|---|---|
| 8 | 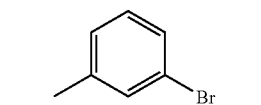 | F: 323 |
| 9 | 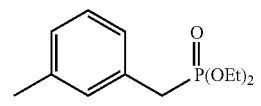 | F: 310 |
| 10 | 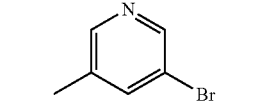 | F: 381 |
| 11 | 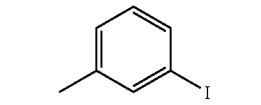 | F: 311 |
| 12 | 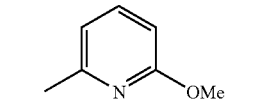 | F: 357 |
| 13 | 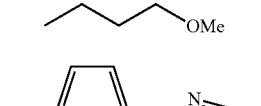 | F: 262 |
| 14 |  | F: 227 |
| 15 | 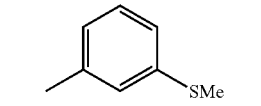 | N1: 7.37(1H, ddd, J=7.5, 4.7, 1.1Hz), 7.59(1H, d, J=9.7Hz), 8.00(1H, d, J=4.0Hz) |
| 16 | 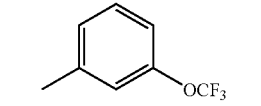 | F: 277 |
| 17 | 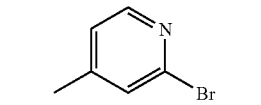 | F: 315 |
| 18 | 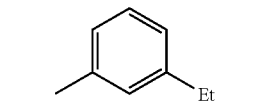 | F: 312 |
| 19 | 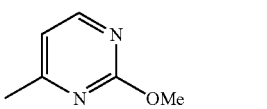 | F: 259 |
TABLE 1-continued
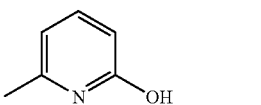
| Rex | —E—R | Dat |
|---|---|---|
| 20 | 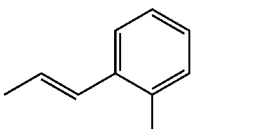 | F: 263 |
| 21 | 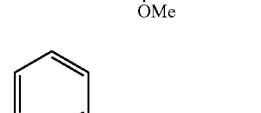 | F: 248 |
| 22 | 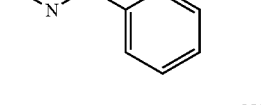 | F: 287 |
| 23 | 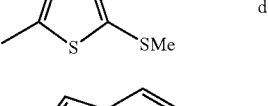 | F: 308 |
| 24 | 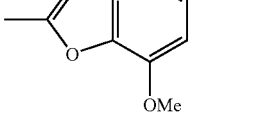 | N1: 2.64(3H, s), 7.28(1H, d, J=3.8Hz), 7.57(1H, d, J=9.7Hz) |
| 25 | 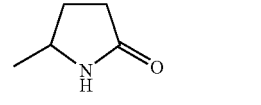 | F: 301 |
| 26 | 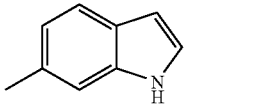 | F: 238 |
TABLE 2
| 27 | 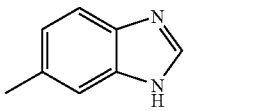 | F: 270 |
|---|---|---|
| 28 | 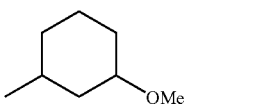 | F: 271 |
| 29 |  | F: 267 |

TABLE 2-continued
| | | |
|---|---|---|
| 30 | 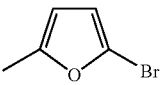 | F: 301 |
| 31 | 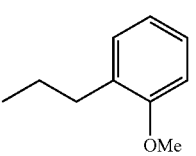 | N1: 1.97–2.04(4H, m), 6.74(1H, dd, J=8.4, 2.4Hz), 8.52(1H, d, J=9.7Hz) |
| 32 | 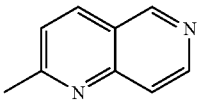 | E: 282 |
| 33 | 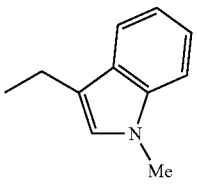 | F: 298 |
| 34 | 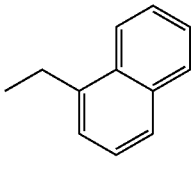 | F: 295 |
| 35 | 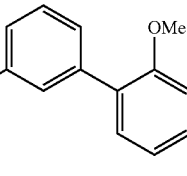 | F: 337 |
| 36 | 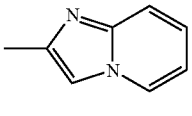 | F: 270 |
| 37 | 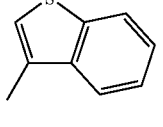 | F: 8.17(1H, d, J=8.6 Hz), 8.62(1H, d, J=9.7 Hz), 8.94(1H, s) |
| 38 | 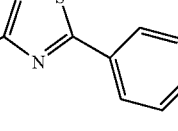 | N1: 7.09(1H, d, J=9.3 Hz), 8.60(1H, d, J=9.7Hz), 8.69(1H, s) |
| 39 | 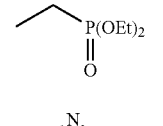 | F: 305 |
| 40 | 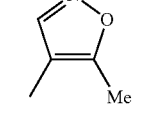 | N1: 2.82(3H, s), 7.58(1H, d, J=9.7Hz), 9.15(1H, s) |
TABLE 2-continued
| | | |
|---|---|---|
| 41 | 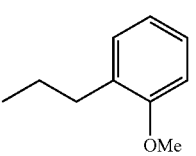 | F: 289 |
| 42 | 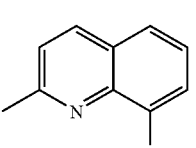 | F: 312 |
| 43 | 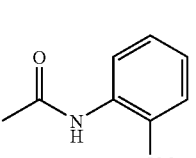 | F: 304 |
| 44 | 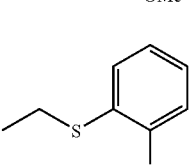 | F: 307 |
| 45 | 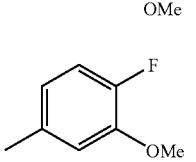 | F: 279 |
| 46 | 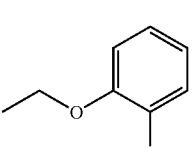 | F: 291 |
| 47 | 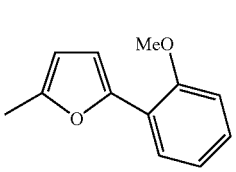 | F: 327 |
| 48 | 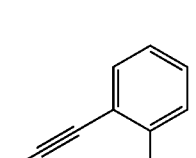 | F: 285 |
| 49 | 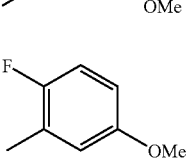 | F: 279 |
| 50 | 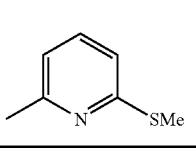 | F: 278 |

TABLE 3

| Ex | RbRaN— | —E—R | Sal | Dat |
|----|--------|------|-----|-----|
| 1 | piperidinyl | 3-cyanophenyl | | M: 200–202 |
| 2 | N-methyl-N-cyclopentyl-methylamino | 3-methoxyphenyl | | M: 136–137<br>N1: 2.52(3H, s), 3.86(3H, s), 8.03(1H, d, J=7.9Hz) |
| 3 | azepan-1-yl | 1-methyl-1H-indol-2-yl | | M: 151–152 |
| 4 | piperidinyl | 3-acetamidophenyl | | M: 210–212 |
| 5 | piperidinyl | 1-(methylsulfonyl)piperidin-3-yl | | M: 207–208 |
| 6 | 2-methoxyphenyl | 3-methoxyphenyl | | M: 153–154 |
| 7 | 2-(piperidin-1-yl)ethoxy | 6-methoxy-2-methylpyridin-3-yl | 2HCl | N1: 4.00(3H, s), 4.82(2H, t, J=4.6Hz), 8.42(1H, d, J=9.8Hz) |
| 8 | azocan-1-yl | 6-methoxypyridin-2-yl | | M: 168–169<br>N1: 1.76(4H, br s), 3.98(3H, s), 6.94(1H, d, J=8.3Hz) |
| 9 | piperidinyl | 3-carbamoylphenyl | | M: 254–257(d) |
| 10 | piperidinyl | 3-(methylsulfonyl)phenyl | | M: 259–260 |

TABLE 3-continued
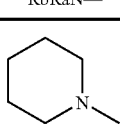
(I)
| Ex | RbRaN— | —E—R | Sal | Dat |
|----|--------|------|-----|-----|
| 11 | 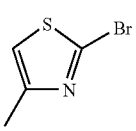 | 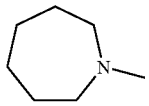 | | N1: 1.65(4H, br s), 8.15(1H, d, J=10.3Hz), 8.67(1H, s) |
| 12 | 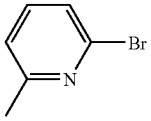 | 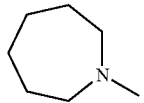 | | M: 151–152<br>N1: 1.80(4H, br s), 7.34(1H, d, J=10.2Hz), 7.75(1H, d, J=7.8Hz) |
TABLE 4
| 13 | 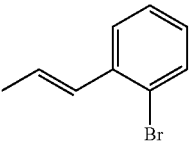 | 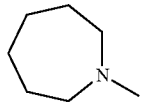 | | M: 180–182 |
| 14 | 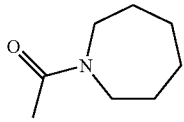 | 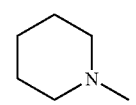 | | N1: 3.55–3.70(6H, m), 7.29(1H, d, J=9.8Hz), 8.08(1H, d, J=10.2Hz) |
| 15 | 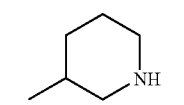 | 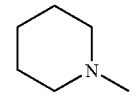 | | F: 421 |
| 16 | 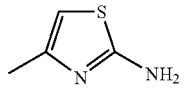 | 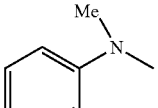 | | F: 302 |
| 17 | 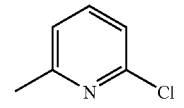 | 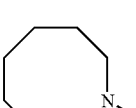 | | F: 337 |
| 18 | 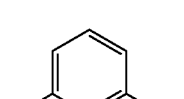 | 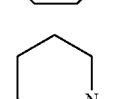 | | F: 343 |
| 19 |  | 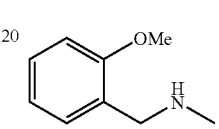 | | F: 297 |
| 20 | 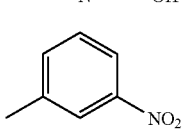 | | | M: 235–236 |

TABLE 4-continued
| | | | |
|---|---|---|---|
| 21 | 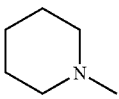 | 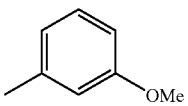 | M: 165–166<br>N1: 3.85(3H, s), 7.07(1 H, dd, J=7.9, 2.4Hz), 7.43 (1H, d, J=10.2Hz) |
| 22 | 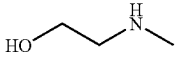 | 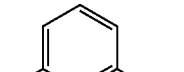 | M: 307–310 |
| 23 | 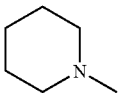 | 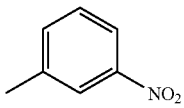 | M: 207–208<br>N1: 1.68(6H, br), 7.50(1H, d, J=10Hz), 9.49(1H, t, J=2.0Hz) |
| 24 | 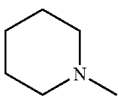 | 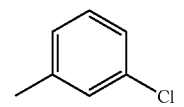 | M: 168–169 |
| 25 | 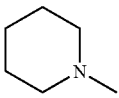 | 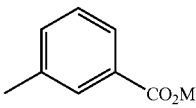 | M: 218–220 |
| 26 | 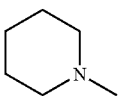 | 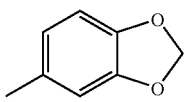 | M: 167–169 |
| 27 | 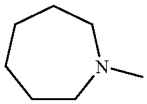 | 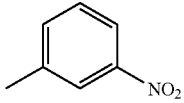 | M: 184–186 |
| 28 | 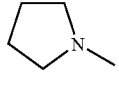 | 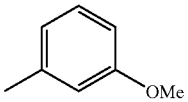 | M: 189–191 |
TABLE 5
| | | | |
|---|---|---|---|
| 29 | 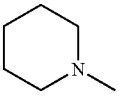 | 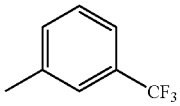 | M: 165–167 |
| 30 | 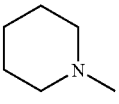 | 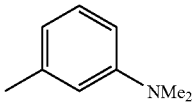 | M: 175–176 |
| 31 | 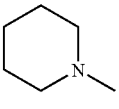 | 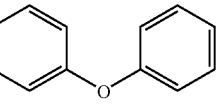 | M: 135–136 |
| 32 | 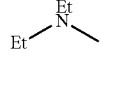 | 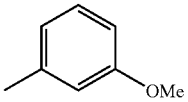 | M: 127–128 |

TABLE 5-continued
| | | | |
|---|---|---|---|
| 33 | 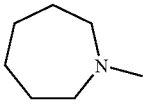 | 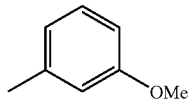 | M: 172–173<br>N1: 3.85(3H, s), 7.27(1H, d, J=10.4Hz), 7.48 (1H, t, J=8.1Hz) |
| 34 | 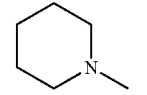 | 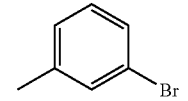 | M: 152–153<br>N1: 1.66(6H, br s), 8.13(1H, d, J=10.3Hz), 8.69(1H, s) |
| 35 | 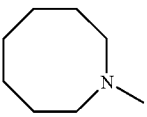 | 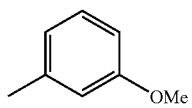 | M: 138–139<br>N1: 1.79(4H, br s), 3.85(3H, s), 7.24(1H, d, J=10.2Hz) |
| 36 | 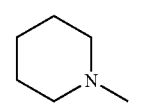 | 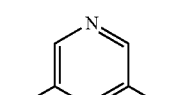 | M: 181–182 |
| 37 | 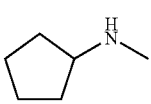 | 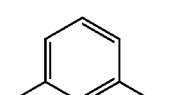 | M: 226–228 |
| 38 | 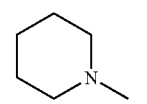 | 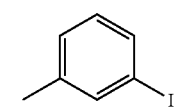 | M: 158–159<br>N1: 1.66(6H, br s), 8.12(1H, d, J=10.2Hz), 8.92(1 H, s) |
| 39 | 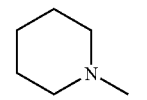 | 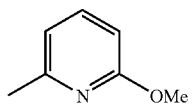 | M: 163–164<br>N1: 3.97(3H, s), 6.94(1H, d, J=7.8Hz), 7.45(1H, d, J=10.2Hz) |
| 40 | 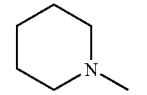 | 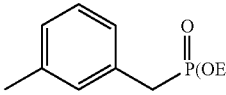 | M: 123–124 |
| 41 | 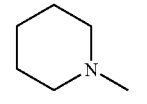 | 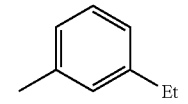 | M: 152–153 |
| 42 | 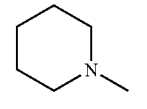 | 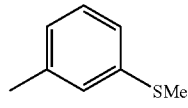 | M: 185–186<br>N1: 2.56(3H, s), 7.43(1H, d, J=10.2Hz), 8.38(1H, s) |
| 43 | 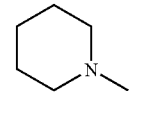 | 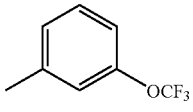 | M: 155–156 |
TABLE 6
| | | | |
|---|---|---|---|
| 44 | 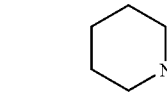 | 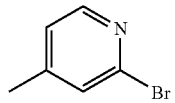 | M: 248–249<br>N1: 1.67(6H, br s), 7.54(1H, d, J=10.3Hz), 8.65(1H, s) |
| 45 | 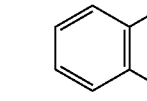 | 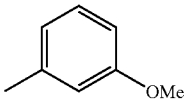 | M: 149–150<br>N1: 3.92(3H, s), 4.81(2H, s), 8.05(1H, d, J=7.8Hz) |

TABLE 6-continued

| # | Amine | Aryl | Data |
|---|---|---|---|
| 46 | N-methylpiperidine | butyl-OMe | M: 104–105 |
| 47 | N-methylpiperidine | 3-methoxy-N-methylaniline | M: 192–193 |
| 48 | 3,5-dimethyl-1-methylpiperidine | 6-methyl-2-methoxypyridine | F: 339<br>N1: 0.91(6H, d, J=6.3Hz), 3.99(3H, s), 8.13(1H, d, J=10.2Hz) |
| 49 | 1'-methyl-[1,4'-bipiperidine] | 6-methyl-2-methoxypyridine | N1: 3.97(3H, s), 6.95(2H, dd, J=7.8, 1.5Hz), 8.14(1H, d, J=10.3Hz) |
| 50 | 1-methyl-1,2,3,6-tetrahydropyridine | 6-methyl-2-methoxypyridine | M: 135–136<br>N1: 3.98(3H, s), 5.82(1H, d, J=10.2Hz), 6.95(1H, d, J=7.9Hz) |
| 51 | 3-(4-methylpiperazin-1-yl)propan-1-ol | 6-methyl-2-methoxypyridine | N1: 3.97(3H, s), 4.44(1H, br s), 8.18(1H, d, J=10.2Hz) |
| 52 | ethyl 4-methylpiperazine-1-carboxylate | 6-methyl-2-methoxypyridine | N1: 1.21(3H, t, J=6.8Hz), 3.97(3H, s), 8.22(1H, d, J=10.3Hz) |
| 53 | methyl 1-methylpyrrolidine-2-carboxylate | 6-methyl-2-methoxypyridine | N1: 3.58(3H, s), 3.97(3H, s), 8.25(1H, d, J=10.3Hz) |
| 54 | 1-methylazepane | 6-methyl-2-methoxypyridine | M: 118–119<br>N1: 1.51(4H, br s), 3.97(3H, s), 6.94(1H, d, J=8.3 HZ) |
| 55 | 1-methylazepane | 2-methyl-5-bromofuran | M: 196–197<br>N1: 1.79(4H, br s), 6.90(1H, d, J=3.4Hz), 7.30(1H, d, J=10.2Hz) |
| 56 | 1-methylazepane | 2-methyl-5-methylthiothiophene | M: 133–135 |
| 57 | 1-methylazepane | 2-methyl-7-methoxybenzofuran | M: 244–246 |

TABLE 7
| 58 | 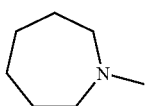 | 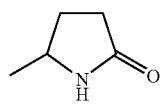 | M: 226–228 |
| 59 | 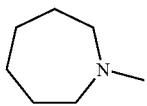 | 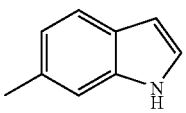 | M: 283–284 |
| 60 | 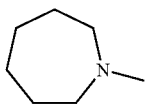 | 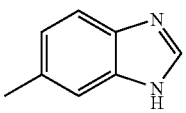 | M: 307–309 |
| 61 | 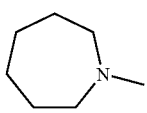 | 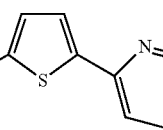 | M: 196–197 |
| 62 | 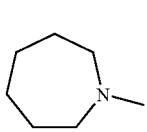 | 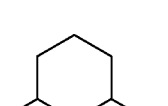 | N1: 3.6–3.7(4H, m), 7.18(1H, d, J=10.3Hz), 7.96(1H, d, J=10.3Hz) |
| 63 | 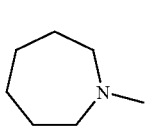 | 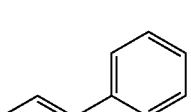 | M: 154–155<br>N1: 3.87(3H, s), 8.05(1H, d, J=9.6Hz), 8.52(1H, d, J=16.8Hz) |
| 64 | 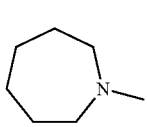 | 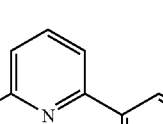 | M: 191–192 |
| 65 | 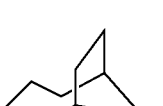 | 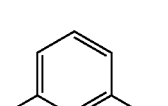 | F: 337<br>N1: 3.36(3H, s), 4.56(2H, br s), 8.15(1H, d, J=9.8Hz) |
| 66 | 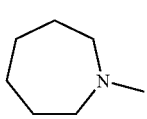 | 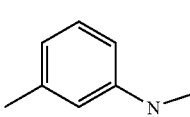 | M: 215–216 |
| 67 | 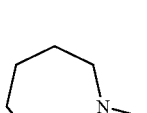 | 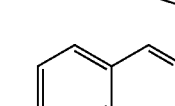 | M: 270–271<br>N1: 3.74(4H, t, J=6.1Hz), 7.40(1H, d, J=10.2Hz), 9.47(1H, s) |
| 68 | 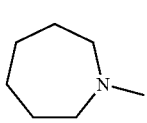 | 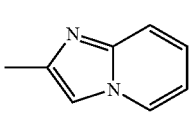 | M: 275–277 |

TABLE 7-continued
| 69 | 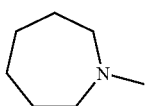 | 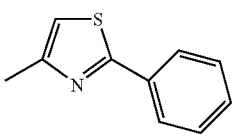 | N1: 3.76(4H, t, J=6.1Hz), 7.34(1H, d, J=10.4Hz), 8.70(1H, s) |
| --- | --- | --- | --- |
| 70 | 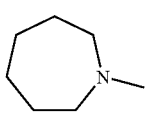 | 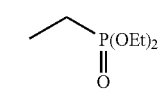 | M: 98–99 |
TABLE 8
| 71 | 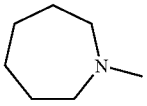 | 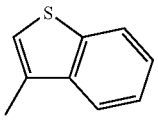 | M: 202–203 |
| --- | --- | --- | --- |
| 72 | 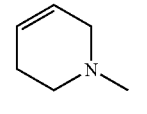 | 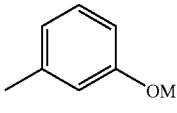 | M: 175–176<br>N1: 2.28(2H, br s), 3.86(3H, s), 5.84(1H, d, J=10.3Hz) |
| 73 | 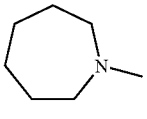 | 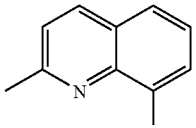 | M: 181–182 |
| 74 | 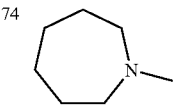 | 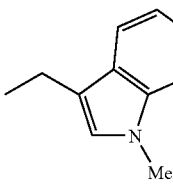 | M: 152–153 |
| 75 | 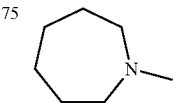 | 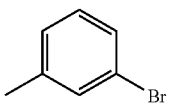 | M: 157–158<br>N1: 1.82(4H, br s), 8.12(1H, d, J=10.2Hz), 8.78(1H, s) |
| 76 | 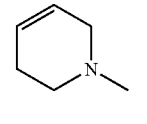 | 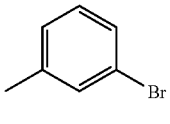 | M: 171–172<br>N1: 2.28(2H, br s), 5.84(1H, d, J=10.3Hz), 8.64(1H, s) |
| 77 | 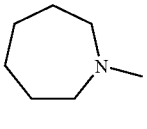 | 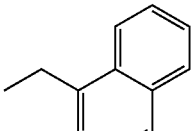 | N1: 3.60(4H, t, J=6.1Hz), 4.79(2H, s), 7.15(1 H, d, J=10.2Hz) |
| 78 | 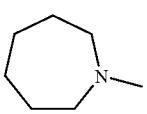 | 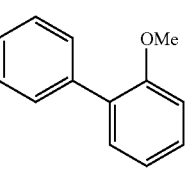 | M: 174–175 |

TABLE 8-continued

| 79 | [azepane-N-CH2-] | [2-ethoxy-6-methoxyphenyl] | F: 354<br>N1: 3.71(1H, s), 5.41 (2H, s), 8.05(1H, d, J=10.2Hz) |
| 80 | [azepane-N-CH2-] | [5-(2-methoxyphenyl)-4-methoxyfuran-2-yl] | M: 187–189 |
| 81 | [azepane-N-CH2-] | [2-methoxyphenyl ethynyl] | M: 126–127 |
| 82 | [azepane-N-CH2-] | [N-(2-methoxyphenyl)acetamide] | N1: 3.88(3H, s), 7.43(1H, d, J=10.2Hz), 10.74(1H, br s) |
| 83 | [azepane-N-CH2-] | [2-methoxyphenyl ethylthio] | M: 116–117 |
| 84 | [azocane-N-CH2-] | [3-bromophenyl] | M: 161–163<br>N1: 1.82(4H, br s), 7.28(1H, d, J=10.2Hz), 8.42(1H, d, J=7.8Hz) |

TABLE 9

| 85 | [piperidine-N-CH2-] | [4-fluoro-3-methoxyphenyl] | F: 328<br>N1: 1.65(4H, br s), 3.95(3H, s), 8.12(1H, d, J=10.3Hz) |
| 86 | [piperidine-N-CH2-] | [3-fluoro-4-methoxyphenyl] | F: 328<br>N1: 3.81(3H, s), 7.51(1H, dd, J=5.4, 3.0Hz), 8.13(1H, d, J=10.3Hz) |
| 87 | [quinuclidine-N-CH2-] | [3-bromophenyl] | M: 207–210<br>N1: 4.56(2H, br s), 7.33(1H, d, J=10.1Hz), 8.42(1H, dd, J=7.8, 1.0Hz) |
| 88 | [3-hydroxypiperidine-N-CH2-] | [6-methoxypyridin-2-yl] | N1: 3.98(3H, s), 4.89(1H, d, J=4.4Hz), 8.15(1H, d, J=10.3Hz) |
| 89 | [quinuclidine-N-CH2-] | [6-(methylthio)pyridin-2-yl] | M: 168–171<br>N1: 2.62(3H, s), 4.55 (2H, br s), 7.33(1H, d, J=10.2Hz) |

TABLE 9-continued

| 90 | [bicyclic N-methyl amine structure] | [6-methoxy-2-methylpyridine] | F: 351<br>N1: 3.79(4H, d, J=4.0Hz), 3.97(3H, s), 8.12(1H, d, J=10.2Hz) |
|---|---|---|---|
| 91 | EtO₂C–O–[piperidine]–N | [6-methoxy-2-methylpyridine] | M: 108–110 |
| 92 | 3-fluoro-1-methylpiperidine | [6-methoxy-2-methylpyridine] | M: 151–153<br>N1: 4.86(1H, dm J=46.9Hz), 3.98(3H, s), 7.49(1H, d, J=10.3Hz) |
| 93 | 4-fluoro-1-methylpiperidine | [6-methoxy-2-methylpyridine] | M: 154–157<br>N1: 3.97(3H, s), 4.93(1H, dm, J=48.4Hz), 7.50(1H, d, J=10.3Hz) |
| 94 | [bicyclic N-methyl amine] | [6-methoxy-2-methylpyridine] | F: 337<br>N1: 3.04(2H, d, J=11.8Hz), 3.97(3H, s), 8.13(1H, d, J=10.3Hz) |
| 95 | 4,4-difluoro-1-methylpiperidine | [6-methoxy-2-methylpyridine] | M: 178–180<br>N1: 2.06–2.16(4H, m), 3.97(3H, s,), 8.22(1 H, d, 10.4Hz) |
| 96 | 3,3-difluoro-1-methylpiperidine | [6-methoxy-2-methylpyridine] | M: 199–202<br>N1: 2.06–2.16(2H, m), 3.99(3H, s), 7.56(1H, d, J=10.3Hz) |
| 97 | H₂NOC–[1-methylpiperidin-3-yl] | [6-methoxy-2-methylpyridine] | N1: 3.96(3H, s), 4.30(2H, d, J=12.2Hz), 8.15(1H, d, J=10.3Hz) |

TABLE 10

| 98 | 4-phenyl-4-cyano-1-methylpiperidine | [6-methoxy-2-methylpyridine] | N1: 3.97(3H, s), 4.51 (2H, d, J=14.1Hz), 8.24(1H, d, J=10.2Hz) |
|---|---|---|---|
| 99 | 4-benzyl-4-hydroxy-1-methylpiperidine | [6-methoxy-2-methylpyridine] | N1: 3.04(2H, d, J=11.8Hz), 3.97(3H, s), 8.13(1H, d, J=10.3Hz) |
| 100 | [N-methyl bicyclic amine] | [3-methoxytoluene] | M: 167–168<br>N1: 3.85(3H, s), 4.58(2H, m), 8.01(1H, d, J=7.8Hz) |

TABLE 10-continued
| 101 | 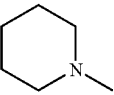 | 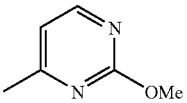 | M: 214–216(d) |
| 102 | 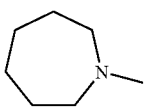 | 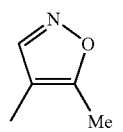 | N1: 2.84(3H, s), 3.70(4H, t, J=5.9Hz), 7.29(1H, d, J=10.4Hz) |
| 103 | 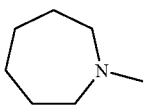 | 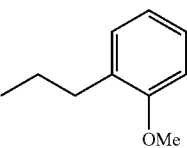 | M: 104–106<br>N1: 3.12(2H, t, J=7.2Hz), 3.68(3H, s), 7.66(1H, d, J=10.4Hz) |
| 104 | 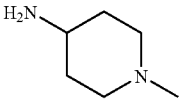 | 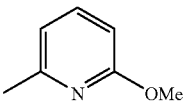 | N1: 3.99(3H, s), 4.34(2H, d, J=13.2Hz), 7.59(1H, d, J=10.2Hz) |
| 105 | 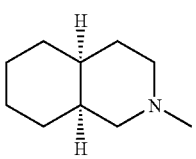 | 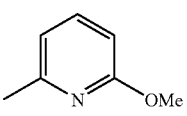 | N1: 4.00(3H, s), 7.02(1H, d, J=7.8Hz), 8.19(1H, d, J=10.3Hz) |
| 106 | 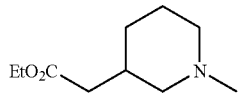 | 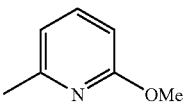 | N1: 1.17(3H, t, J=7.1Hz), 4.01(3H, s), 8.29(1H, d, J=10.2Hz) |
| 107 | 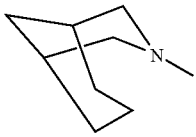 | 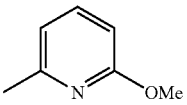 | F: 351<br>N1: 2.07(1H, br s), 4.01 (3H, s), 8.24(1H, d, J=10.3Hz) |
| 108 | 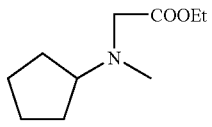 | 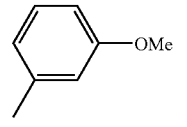 | M: 133–135 |
| 109 | 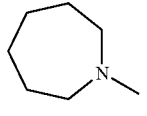 | 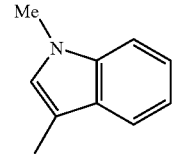 | M: 226–227 |
| 110 | 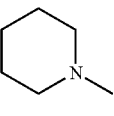 | 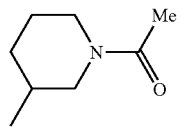 | M: 178–179 |
| 111 | 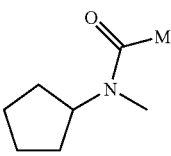 | 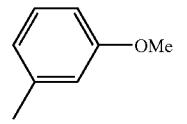 | M: 175–177 |

TABLE 11
| | | | |
|---|---|---|---|
| 112 | 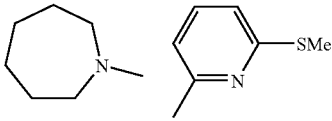 | 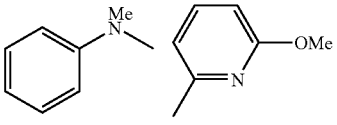 | M: 124–125<br>N1: 1.77(4H, br s), 2.62(3H, s),<br>7.31(1H, d, J=10.3Hz) |
| 113 | 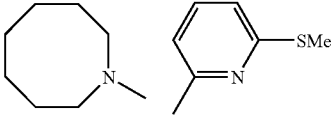 | 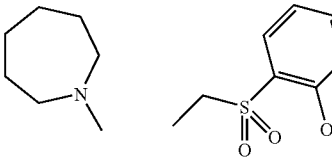 | F: 337<br>N1: 3.45(3H, s), 4.00(3H, s),<br>8.03(1H, d, J=10.3Hz) |
| 114 | 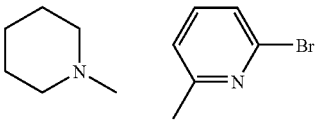 | 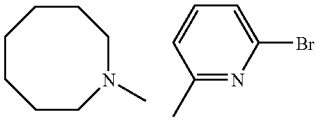 | M: 139–141<br>N1: 7.73–1.84(4H, m), 2.62(3H, s),<br>7.28(1H, d, J=10.3Hz) |
| 115 | 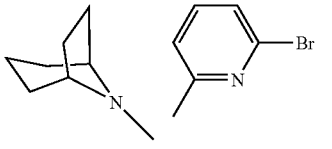 | 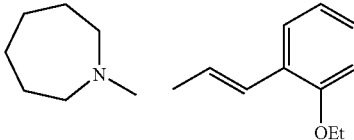 | M: 189–191 |
| 116 | 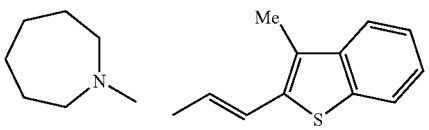 | 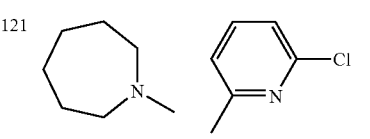 | M: 176–177<br>N1: 1.63(6H, br s), 7.48(1H, d,<br>J=10.2Hz), 7.76(1H, d,<br>J=7.8Hz) |
| 117 | 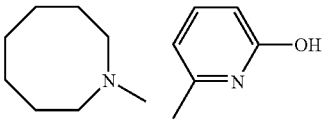 |  | M: 169–171<br>N1: 1.80(4H, br s), 7.31(1H, d,<br>J=10.3Hz), 8.47(1H, d,<br>J=7.6Hz) |
| 118 |  |  | F: 384<br>N1: 4.57(2H, br s), 7.35(1H, d,<br>J=10.0Hz), 8.49(1H, d,<br>J=7.8Hz) |
| 119 |  |  | F: 364<br>N1: 1.42(3H, t, J=6.9Hz), 7.53(1H,<br>d, J=16.6Hz), 8.06(1H, d,<br>J=10.3Hz) |
| 120 |  |  | M: 239–241 |
| 121 |  |  | F: 329 |
| 122 |  |  | F: 325 |

TABLE 11-continued
| 123 | 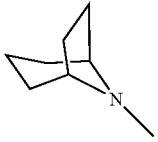 | 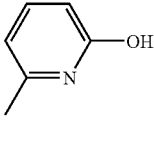 | F: 323 |
TABLE 12
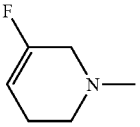
(I)
| No. | RbRaN— | —E—R |
|---|---|---|
| 1 | 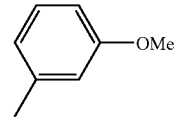 | 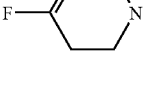 |
| 2 | 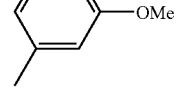 | 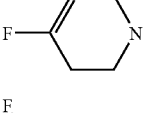 |
| 3 | 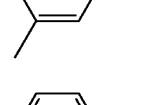 | 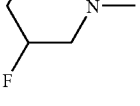 |
| 4 | 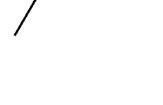 | 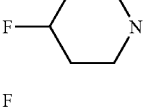 |
| 5 | 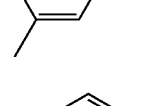 | 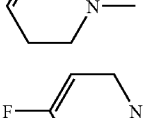 |
| 6 | 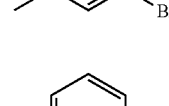 | 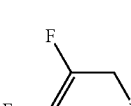 |
| 7 | 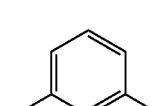 | 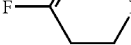 |
| 8 | 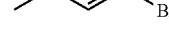 | 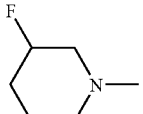 |
TABLE 12-continued
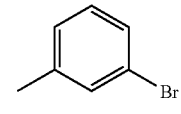
(I)
| No. | RbRaN— | —E—R |
|---|---|---|
| 9 | 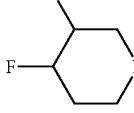 | 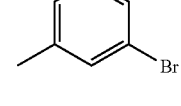 |
| 10 | 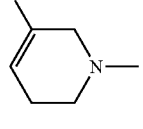 | 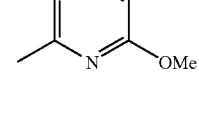 |
| 11 | 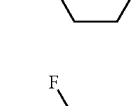 | 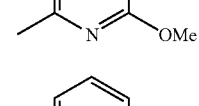 |
| 12 | 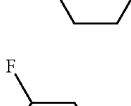 | 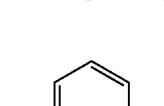 |
| 13 | 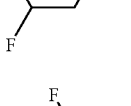 | 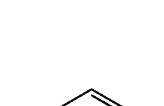 |
| 14 | 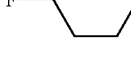 | 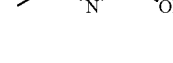 |
| 15 |  |  |

TABLE 12-continued

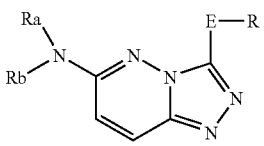

| No. | RbRaN— | —E—R |
|---|---|---|
| 16 | F, tetrahydropyridine N— | pyridine-Br |
| 17 | F-piperidine-N— | pyridine-Br |
| 18 | F, F-tetrahydropyridine-N— | pyridine-Br |
| 19 | F, F-piperidine-N— | pyridine-Br |
| 20 | F, F-piperidine-N— | pyridine-Br |

What is claimed is:

1. A compound represented by the formula (I):

(I)

or a pharmaceutically acceptable salt thereof,
wherein
Ra and Rb taken together with an adjacent N atom represent a 4- to 8-membered saturated or partially unsaturated heterocyclic ring containing 1 to 2 nitrogen atoms as heteroatoms, said heterocyclic ring may be fused with a benzene ring or a cycloalkyl ring and may have a bridge and may form a spiro ring, and said heterocyclic ring may have 1 to 5 substituents selected from Group B,
wherein Group B consists of a lower alkyl which may have 1 to 4 substituents selected from Group G, halogen, NR$^1$R$^2$, —NR$^1$CO-lower alkyl, NO$_2$, CN, OR$^1$, —O-(lower alkyl having 1 to 4 substituents selected from Group G), SR$^1$, —S-halogeno-lower alkyl, —O—CO-lower alkyl, COOR$^1$, COR$^1$, CONR$^1$R$^2$, SO-lower alkyl, SO$_2$-lower alkyl, SO$_2$NR$^1$R$^2$, P(=O)(OR$^1$)$_2$, —O—CH$_2$—O—, —O—(CH$_2$)$_2$—O—, aryl which may have 1 to 4 substituents selected from Group D, heteroaryl which may have 1 to 4 substituents selected from Group D, —O—(aryl which may have 1 to 4 substituents selected from Group D), 4- to 8-membered monocyclic saturated or partially unsaturated heterocyclic ring which may have 1 to 4 substituents selected from Group D, cycloalkyl and —O-cycloalkyl;
Group D consists of a lower alkyl, halogen, halogeno-lower alkyl, NR$^1$R$^2$, NO$_2$, CN, OR$^1$ and SR$^1$; Group G consists of a halogen, NR$^1$R$^2$, CN, COOR$^1$, OR$^1$, SR$^1$, 4- to 8-membered monocyclic saturated or partially unsaturated heterocyclic ring which may have 1 to 4 substituents selected from Group D, aryl which may have 1 to 4 substituents selected from Group D and heteroaryl which may have 1 to 4 substituents selected from Group D;
E: a single bond, C$_{1-3}$ alkylene, vinylene (—C=C—), ethynylene (—C≡C—), CO, NR$^3$, CH$_2$—J, CONR$^4$ or NR$^5$CO,
J: O, S, NR$^6$, CO, SO or SO$_2$,
R: an aryl optionally substituted with 1 to 5 substituents selected from Group B, a heteroaryl optionally substituted with 1 to 5 substituents selected from Group B, a cycloalkyl optionally substituted with 1 to 5 substituents selected from Group B, a cycloalkenyl optionally substituted with 1 to 5 substituents selected from Group B or a 4- to 8-membered monocyclic saturated or partially saturated heterocyclic ring optionally substituted with 1 to 5 substituents selected from Group B,
R$^1$ to R$^6$ the same or different and each denotes H or lower alkyl;
with the proviso that the following compounds are excluded:
(1) a compound wherein Ra and Rb taken together with an adjacent N atom represent a piperidino, E is a single bond and R is a piperidino, unsubstituted phenyl, p-(trifluoromethyl)phenyl, p-chlorophenyl or o-nitrophenyl,
(2) a compound wherein Ra and Rb taken together with an adjacent N atom represent a 4-methyl-1-piperazinyl, E is a single bond, and R is an unsubstituted phenyl, p-methylphenyl, m-methylphenyl, p-methoxyphenyl, m-chlorophenyl, p-chlorophenyl or m-nitrophenyl, and
(3) a compound wherein R is an imidazolyl optionally substituted with 1 to 5 substituents selected from Group B, 5-nitro-2-furyl or 5-nitro-2-thienyl.

2. The compound according to claim 1 or a pharmaceutically acceptable salt thereof,
wherein E is a single bond, C$_{1-3}$ alkylene, vinylene, ethynylene, CONH, CH$_2$NH, CH$_2$O or CH$_2$S; R is an aryl which may have 1 to 5 substituents selected from Group B or heteroaryl which may have 1 to 5 substituents selected from Group B.

3. The compound according to claim 2 or a pharmaceutically acceptable salt thereof, wherein E is a single bond, C$_{1-3}$ alkylene, vinylene or ethynylene; R is an aryl having 1 to 5 substituents selected from Group B1 or heteroaryl having 1 to 5 substituents selected from Group B1; Group B1 consists of a lower alkyl, halogeno-lower alkyl, halogen, NR$^1$R$^2$, NO$_2$, CN, OR$^1$, —O-halogeno-lower alkyl, SR$^1$, COOR$^1$, CONR$^1$R$_2$, SO$_2$-lower alkyl, 4- to 8-membered monocyclic saturated or partially unsaturated heterocyclic ring, phenyl and phenoxy.

4. The compound according to claim 3 or a pharmaceutically acceptable salt thereof, wherein -NRaRb is a 4- to 8-membered monocyclic saturated or partially unsaturated heterocyclic ring which may have one N atom as a heteroatom and may have a bridge, and may have 1 to 2 substituents selected from a lower alkyl, halogen, $OR^1$ and $COOR^1$; E is a single bond; R is a phenyl having a substituent in its m-position selected from a halogen, O-lower alkyl and S-lower alkyl or a pyridyl having a substituent in its 6-position selected from a halogen, O-lower alkyl and S-lower alkyl.

5. The compound according to claim 1 or a pharmaceutically acceptable salt thereof selected from the group consisting of 6-azocan-1-yl-3-(6-methoxypyridin-2-yl)-1,2,4-triazolo[4,3-b]pyridazine, 6-azepan-1-yl-3-(6-bromopyridin-2-yl-1,2,4-triazolo[4,3-b]pyridazine, 3-(3-methoxyphenyl)-6-(piperidin-1-yl)-1,2,4-triazolo[4,3-b]pyridazine, 3-(3-bromophenyl)-6-(piperidin-1-yl)-1,2,4-triazolo[4,3-b]pyridazine, 6-azepan-1-yl-3-(6-methoxypyridin-2-yl)-1,2,4-triazolo[4,3-b]pyridazine, 6-(4-fluoropiperidin-1-yl)-3-(6-methoxypyridin-2-yl)-1,2,4-triazolo[4,3-b]pyridazine, 6-(3-azabicyclo[3.2.1]octan-3-yl)-3-(6methoxypyridin-2-yl)-1,2,4-triazolo[4,3-b]pyridazin, 6-(4,4-difluoropiperidin-1-yl)-3-(6-methoxypyridin-2-yl) -1,2,4-triazolo[4,3-b]pyridazine, 6-(3,3-difluoropiperidin-1-yl)-3-(6methoxypyridin-2-yl) -1,2,4-triazolo[4,3-b]pyridazine, 6-azocan-1-yl-3-(6-bromopyridin-2-yl)-1,2,4-triazolo [4,3-b]pyridazine, and 6-(8-azabicyclo[3.2.1]octan-8-yl)-3-(6-bromopyridin-2-yl) -1,2,4-triazolo[4,3-b] pyridazine.

6. A pharmaceutical composition comprising the compound according to claim 1 or a pharmaceutically acceptable salt thereof and a pharmaceutically acceptable carrier.

7. A method for stimulating bone formation in a mammalian animal, comprising administering an effective amount of the compound according to claim 1 or a pharmaceutically acceptable salt thereof to the mammalian animal.

* * * * *